United States Patent
Pass et al.

(10) Patent No.: US 9,157,080 B2
(45) Date of Patent: Oct. 13, 2015

(54) COMPOSITIONS AND METHODS FOR TREATMENT, DIAGNOSIS AND PROGNOSIS OF MESOTHELIOMA

(75) Inventors: Harvey Pass, Bronxville, NY (US); Moshe Hoshen, Jerusalem (IL); Sergey Ivanov, Brentwood, TN (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/395,004

(22) PCT Filed: Sep. 6, 2010

(86) PCT No.: PCT/IL2010/000728
§ 371 (c)(1),
(2), (4) Date: Mar. 28, 2012

(87) PCT Pub. No.: WO2011/030334
PCT Pub. Date: Mar. 17, 2011

(65) Prior Publication Data
US 2012/0177599 A1    Jul. 12, 2012

Related U.S. Application Data

(60) Provisional application No. 61/240,663, filed on Sep. 9, 2009.

(51) Int. Cl.
*C12N 15/11* (2006.01)
*C12N 15/113* (2010.01)
*C12Q 1/68* (2006.01)

(52) U.S. Cl.
CPC ............. *C12N 15/113* (2013.01); *C12Q 1/6886* (2013.01); *C12N 2310/141* (2013.01); *C12N 2320/31* (2013.01); *C12Q 2600/118* (2013.01); *C12Q 2600/158* (2013.01); *C12Q 2600/178* (2013.01)

(58) Field of Classification Search
CPC ...................... C12N 2310/141; C12N 15/113
See application file for complete search history.

(56) References Cited

U.S. PATENT DOCUMENTS

| | | |
|---|---|---|
| 6,271,002 B1 | 8/2001 | Linsley et al. |
| 6,858,598 B1 | 2/2005 | McKearn et al. |
| 2003/0204075 A9 | 10/2003 | Wang |
| 2003/0219760 A1 | 11/2003 | Gordon et al. |
| 2006/0105360 A1 | 5/2006 | Croce et al. |
| 2009/0131356 A1* | 5/2009 | Bader et al. .................... 514/44 |

FOREIGN PATENT DOCUMENTS

WO    WO2008036776 A2 *    3/2008

OTHER PUBLICATIONS

Breving et al. The International Journal of Biochemistry & Cell Biology 42 (2010) 1316-1329.*
Aisner, Joseph et al., "Malignant Mesothelioma, Current Status and Future Prospects" Chest, vol. 74, No. 4, Oct. 1978, pp. 438-444.
Illei, Peter B. et al., "Homozygous Deletion of CDKN2A and Codeletion of the Methylthioadenosine Phosphorylase Gene in the Majority of Pleural Mesotheliomas," Clinical Cancer Research, vol. 9, No. 6, Jun. 2003, pp. 2108-2113.
International Search Report mailed Feb. 10, 2011 in PCT/IL2010/00728.

* cited by examiner

*Primary Examiner* — Brian Whiteman
(74) *Attorney, Agent, or Firm* — Polsinelli PC; Ron Galant

(57) ABSTRACT

Described herein are compositions and methods for the treatment and diagnosis of mesothelioma, and determination of prognosis of mesothelioma patients after surgical operation. Specifically, the invention relates to microRNA molecules associated with treatment, diagnosis and determination of prognosis of mesothelioma, as well as various nucleic acid molecules relating thereto or derived therefrom.

18 Claims, 20 Drawing Sheets

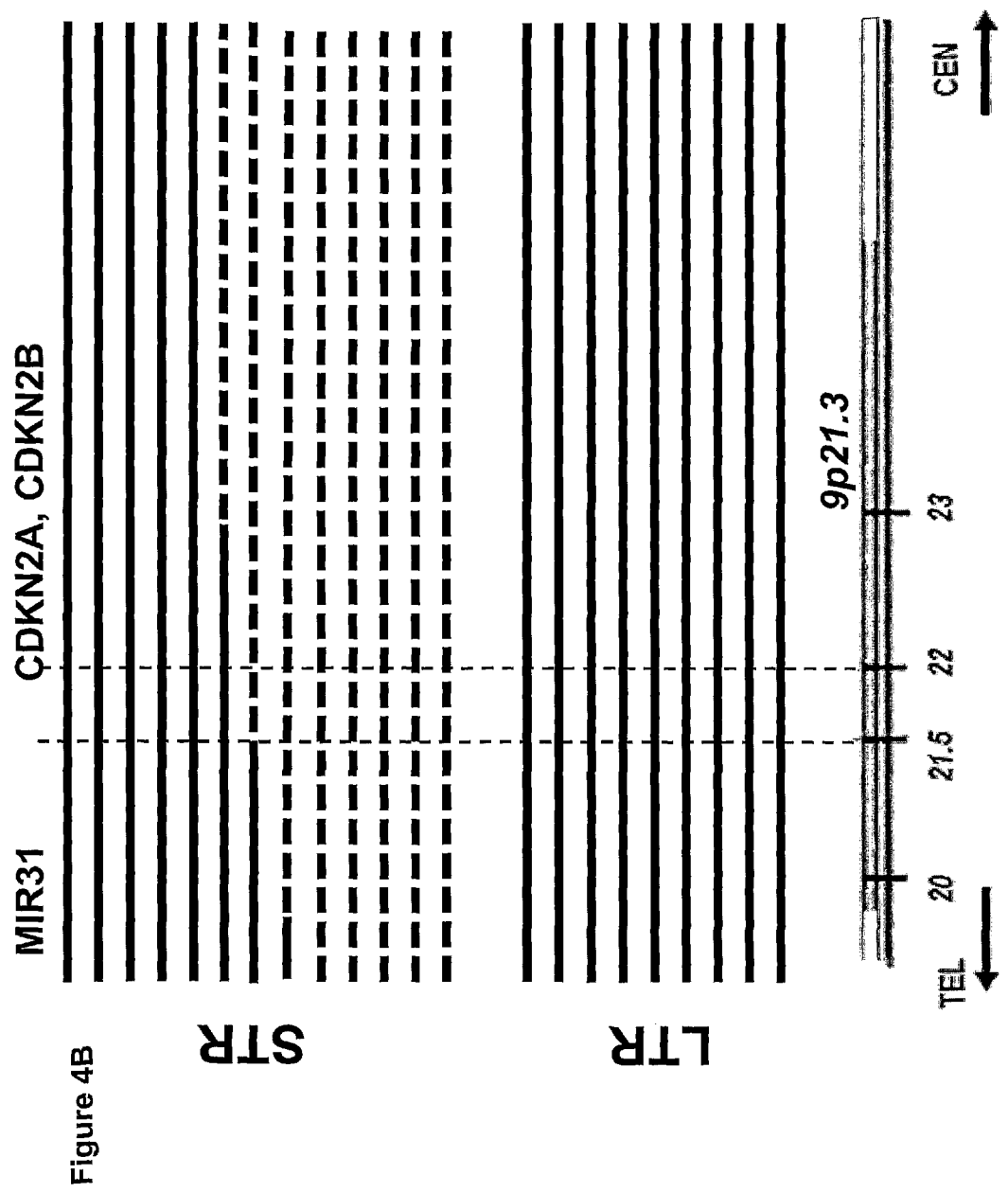

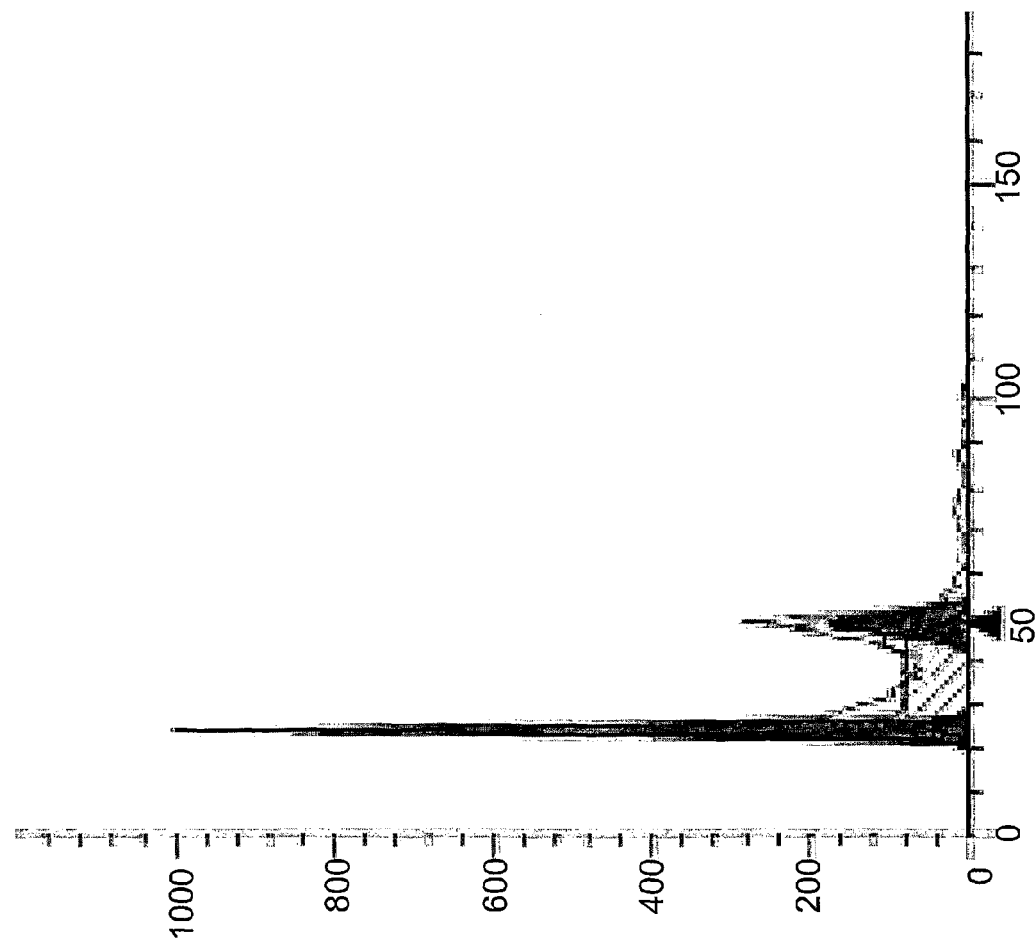

Figure 8A

Site 1

```
CTGAAATGCT-GCCTGTTGCCT
  ||||| || ||||||| ||||
UCGA-UACGGUCGUAGAACGGA
```
pos. 1350-1370
-33.1 Kcal/mol

Site 2

```
TGCTGC-ATGT-AGC-TCTTGCTT
  |||| |||| ||| |||||||
U---CGAUACGGUCGUAGAACGGA
```
pos. 1511-1531
-30.9 Kcal/mol

Site 3

```
TC----TGCCATCTCTGTTTTGCCT
      |||| |  |||| ||||||
UCGAUACGGUCG---UAGAACGGA
```
pos. 3333-3353
-29.1 Kcal/mol

COMPOSITIONS AND METHODS FOR TREATMENT, DIAGNOSIS AND PROGNOSIS OF MESOTHELIOMA

CROSS-REFERENCE TO RELATED APPLICATIONS

This application is the U.S. National Phase of PCT/IL2010/000728, filed Sep. 6, 2010, which claims priority to U.S. Provisional Application No. 61/240,663, filed Sep. 9, 2009, all of which are incorporated herein by reference in entirety.

FIELD OF THE INVENTION

The invention relates to compositions and methods for treatment and diagnosis of mesothelioma, and determination of prognosis of mesothelioma patients after surgical operation. Specifically, the invention relates to microRNA molecules associated with the treatment and determination of prognosis of mesothelioma patients, as well as various nucleic acid molecules relating thereto or derived therefrom.

BACKGROUND OF THE INVENTION

In recent years, microRNAs (miRs, miRNAs) have emerged as an important novel class of regulatory RNA, which has a profound impact on a wide array of biological processes. These small (typically 18-24 nucleotides long) non-coding RNA molecules can modulate protein expression patterns by promoting RNA degradation, inhibiting mRNA translation, and also affecting gene transcription. miRNAs play pivotal roles in diverse processes such as development and differentiation, control of cell proliferation, stress response and metabolism. Recent studies have revealed that miRNA expression in malignant cells can be affected by both genetic and epigenetic events associated with tumor growth. There are currently about 1,100 known human miRNAs. The expression of many of these has been found to be altered in numerous types of human cancer, and in some cases strong evidence has been put forward in support of the conjecture that such alterations may play a causative role in tumor progression via the regulation of tumor suppressors and oncogenes.

Mesothelioma is a tumor that occurs in the mesothelium that covers the surface of the pleura, peritoneum and pericardium that respectively envelop the organs of the chest cavity such as the lungs and heart, and abdominal organs such as the digestive tract and liver. In the case of diffuse pleural mesothelioma, chest pain is caused by invasion of the intercostal nerves on the side of the chest wall pleura, and respiratory and circulatory disorders may occur due to tumor growth and accumulation of pleural fluid in the pleura on the organ side (Takagi, Journal of Clinical and Experimental Medicine, (March Supplement), "Respiratory Diseases", pp. 469-472, 1999). Eventually, there is proliferation into the adjacent mediastinal organs, progressing to direct invasion of the heart or development in the abdominal cavity by means of the diaphragm, or there may be development outside the chest cavity as a result of additional lymphatic or circulatory metastasis.

In the U.S., diffuse pleural mesothelioma is reported to occur in 3,000 persons annually, with the number of cases increasing significantly through the 1980's. The disease is frequently observed in men in their sixties, with the incidence in men being roughly five times that in women. According to recent reports in the U.S. and Europe, the incidence of mesothelioma demonstrates a rapidly increasing trend, and, based on epidemiological statistics from the U.K. in 1995, the number of deaths from mesothelioma is predicted to continue to increase over the next 25 years. In the worst possible scenario, mesothelioma may be found to account for 1% of all deaths among men born in the 1940's.

Numerous different classification schemes for the clinical disease stages have been established for mesothelioma, and since the classification methods differ, comparison of the results of treatment for mesothelioma is difficult (Nakano, Environ Health Prev Med, 2008; 13:75-83).

In addition, malignant mesothelioma (MM) has a causative relationship with exposure to asbestos, and this has also been demonstrated in animal experiments (Tada, Journal of Clinical and Experimental Medicine (March Supplement), "Respiratory Diseases", pp. 406-408, 1999). Asbestos that has been inhaled into the respiratory tract reaches a location directly beneath the pleura where a tumor eventually develops due to chronic irritation for typically 20 years, and this tumor spreads in a thin layer over the entire surface of the pleura. Consequently, although malignant mesothelioma is classified as an asbestos-related disease, not all malignant mesothelioma is caused by asbestos, and well-documented exposure is only observed in about half of all patients. Malignant pleural mesothelioma is resistant to treatment, associated with an extremely poor prognosis, and requires that countermeasures be taken immediately (Nakano, Environ Health Prev Med, 2008; 13: 75-83).

The prognosis for malignant mesothelioma is influenced by the stage of the disease. Surgery, when performed as part of a multimodality therapy with cytotoxic chemotherapy and radiation therapy, as well as adjuvant immunological treatments (e.g., interferon or interleukin) can be an effective treatment, but only in the rare event of diagnosis at an early stage.

In mesothelioma, the 9p21.3 deletions are often homozygous and linked with poor prognosis (Ivanov et al., Int J Cancer 2009; 124:589-599). Two tumor suppressor genes are localized in this area: CDKN2A (cyclin-dependent kinase inhibitor), which encodes the cell cycle inhibitory p16$^{INK4A}$ and p14$^{ARF}$ proteins, and the adjacent CDKN2B (p15$^{INK4B}$) (Ruas and Peters, Biochim Biophys Acta 1998; 1378:F115-177). Combined deficiency of these products may have a synergistic effect in malignant transformation (Krimpenfort et al., Nature 2007; 448:943-946).

Much emphasis has been placed on the discovery and characterization of a unique tumor marker. However, no marker has yet been identified that has adequate sensitivity or specificity to be clinically useful, although a combination of multiple markers has been shown to increase prognostic accuracy. There is an unmet need for identification of specific and accurate markers associated with mesothelioma, especially those which could have prognostic significance in determining the type and extent of therapy necessary or reasonable for survival, and for compositions which could be employed in treating mesothelioma.

SUMMARY OF THE INVENTION

According to some aspects of the present invention, specific nucleic acid sequences (SEQ ID NOS: 1-2) or variants thereof may be used for treatment and determination of the prognosis of mesothelioma in patients suffering from same.

According to one aspect, the present invention provides a method of treating or preventing malignant mesothelioma comprising administering to a subject in need therefore an effective amount of a composition comprising a nucleic acid sequence selected from the group consisting of:
  (a) SEQ ID NOS: 1-2;
  (b) a sequence at least about 80% identical to (a); and
  (c) a fragment thereof.

In one embodiment, the present invention provides for the use of a composition comprising a nucleic acid sequence selected from the group consisting of:
  (a) SEQ ID NO: 1-2;
  (b) a sequences at least about 80% identical to (a);
  (c) a fragment thereof,
for the preparation of a medicament suitable for the treatment or prevention of malignant mesothelioma.

In some embodiments, the methods of the present invention further comprise administering at least one additional therapy. In some embodiments, said additional therapy is a chemotherapeutic agent. In some embodiments, the chemotherapeutic agent is selected from the group consisting of cisplatin, pemetrexed, navelbine, gemcitabine, carboplatin, camptothecins, doxorubicin, cyclophosphamide, etoposide, vinblastine, Actinomycin D and cloposide. In some embodiments, said additional therapy is a small molecule or antibody. In some embodiments, said small molecule or antibody includes but is not limited to vorinostat, PI3 kinase inhibitors, mTOR inhibitors, proteosome inhibitors, vascular targeting agents, angiogenesis inhibitors. In some embodiments, said additional therapy further comprises radiation therapy. In some embodiments, said additional therapy further comprises adjuvant immunological treatments. In other embodiments, said adjuvant immunological treatments may be selected from the group consisting of interferon and interleukin.

In one embodiment, administering results in reduction of tumor size. In one embodiment, administering results in reduction of tumor number. In one embodiment, administering prevents an increase in tumor size. In one embodiment, administering prevents an increase in tumor number. In one embodiment, administering prevents metastatic progression. In one embodiment, administering slows metastatic progression. In one embodiment, administering extends overall survival time of the subject. In one embodiment, administering extends progression-free survival of the subject.

According to another aspect, the present invention provides a method for the diagnosis of mesothelioma in a subject, the method comprising:
  (a) obtaining a biological sample from the subject;
  (b) determining the expression level in said sample of a nucleic acid sequence selected from the group consisting of SEQ ID NOS: 1-2, a sequence having at least about 80% identity thereto, or a fragment thereof; and
  (c) comparing said expression level to a control expression level,
whereby an expression level of said nucleic acid sequence below said control expression level is indicative of mesothelioma in said subject.

According to further aspect, the present invention provides a method for determining the prognosis of malignant mesothelioma in a subject comprising
  (a) obtaining a biological sample from the subject;
  (b) determining an expression level in said sample of a nucleic acid selected from the group consisting of SEQ ID NOS: 1-2, a sequence having at least about 80% identity thereto, or a fragment thereof; and
  (c) comparing said expression level to a threshold expression level,
whereby a decreased expression level relative to said threshold expression level is indicative of poor prognosis in said subject. In some embodiments, the method further comprises determining the presence of a tumor suppressor gene in said sample. In some embodiments, the tumor suppressor gene is selected from the group consisting of CDKN2A and CDKN2B. In some embodiments, said prognosis is the time to relapse of malignant mesothelioma in said subject.

In some embodiments of the present invention, the subject is a human. In some embodiments, the methods of the present invention are used to determine a course of treatment for said subject.

In some embodiments, the biological sample obtained from the subject is selected from the group consisting of bodily fluid, a cell line and a tissue sample. In some embodiments the tissue is a fresh, frozen, fixed, wax-embedded or formalin fixed paraffin-embedded (FFPE) tissue. In some embodiments the tissue is mesothelium. In other embodiments the bodily fluid is serum.

In some embodiments, the expression levels are determined by a method selected from the group consisting of nucleic acid hybridization, nucleic acid amplification, and a combination thereof. In some embodiments, the nucleic acid hybridization is performed using a solid-phase nucleic acid biochip array or in situ hybridization. In one embodiment, the nucleic acid amplification method is real-time PCR. In some embodiment, the RT-PCR method comprises forward and reverse primers. In some embodiments, the forward primer comprises SEQ ID NO: 3 and sequences at least about 80% identical thereto. In some embodiments, the reverse primer comprises SEQ ID NO: 5 and sequences at least about 80% identical thereto. In some embodiments, the nucleic acid comprises a modified nucleobase.

In another aspect, the present invention provides a method of modulating the expression level of a first nucleic acid sequence wherein said nucleic acid comprises a sequence selected from the group consisting of SEQ ID NOS: 28-30 comprising introducing to a subject in need thereof an effective amount of a composition comprising a second nucleic acid sequence selected from the group consisting of:
  (a) SEQ ID NOS: 1-2;
  (b) a sequence at least about 80% identical to (a); and
  (c) a fragment thereof,
  wherein said second nucleic acid modulates the expression of said first nucleic acid.

The invention also provides a kit for determining a diagnosis of mesothelioma, said kit comprising a probe comprising a nucleic acid sequence that is complementary to a sequence selected from the group consisting of SEQ ID NOS: 1-2, a sequence at least about 80% identical thereto, and a fragment thereof. The invention further provides a kit for determining a prognosis of a subject with malignant mesothelioma, said kit comprising a probe comprising a nucleic acid sequence that is complementary to sequences selected from the group consisting of SEQ ID NO: 1-2, a sequence at least about 80% identical thereto, and a fragment thereof. In some embodiments, the kit further comprises forward and reverse primers. In some embodiments, said forward primer comprises SEQ ID NO: 3 and sequences at least about 80% identical thereto. In some embodiments, said reverse primer comprises SEQ ID NO: 5 and sequences at least about 80% identical thereto. In some embodiments, the kit comprises reagents for performing in situ hybridization analysis.

BRIEF DESCRIPTION OF THE DRAWINGS

In FIG. 6A the y-axis depicts the number of cells invaded 48 hours following transfection, based on the results of a matrigel invasion assay. In FIG. 6B the y-axis depicts the percentage of wound closure 24 hours following transfection, based on the results of a scratch (wound healing) assay. In FIG. 6C the y-axis depicts changes in cell density (in arbitrary units) 48 hours following transfection, based on the results of a cell proliferation assay. In FIG. 6D the y-axis depicts number of colonies 21 days following transfection, based on soft agar colony formation assay.

FIGS. 7A-D show the suppressive effects on miR-31 on cell cycle and its potential mediators. 7A-B. Decrease in the number of cells in S-phase and increase in the number of cells in G1 phase upon transfection of HP-1 cells with miR-31 mimic (7B: miR-31) (G1: 80.0%; S: 13.8%; G2/M: 6.3%), as compared to negative control oligonucleotide (7A: CON) (G1: 72.8%; S: 18.8%; G2/M: 8.4%). 7C-D. Introduction of miR-31 inhibitor in H2461 promotes S-phase (7D: miR-31) (G1: 46.4%; S: 34.48%; G2/M: 19.2%) relative to negative control oligonucleotide (7C: CON) (G1: 66.6%; S: 25.1%; G2/M: 8.3%).

FIGS. 8A-E show validation of PPP6C as a miR-31 target. 8A. Three potential binding site sequences for miR-31 in the 3'-UTR of PPP6C (SEQ ID NOS: 28-30). 8B. Three out of four Affymetrix U133 Plus 2.0 probes for PPP6C show downregulation of PPP6C upon transfection of HP-1 cells with miR-31. The y-axis depicts signal intensities in arbitrary units. Gray bar in each set represents cells transfected with miR-31 mimic; dark bar represents lipofectamine only; light bar represents cells transfected with negative control oligonucleotide. 8C. Effects on PPP6C mRNA expression produced by introduction of miR-31 into HP-1 cells and miR-31 inhibitor (INH) into H2461 cells. Signal intensities in arbitrary units are compared. PPIA used as a loading control. 8D. Clinical validation of PPP6C shows up-regulation of the gene in malignant mesothelioma specimens (labeled with "T") as compared to matched mesothelium from healthy peritoneum (labeled with "N"). 8E. Western analysis of miR-31 effects on PPP6C and MCM2 protein levels.

DETAILED DESCRIPTION OF THE INVENTION

Figure 1:
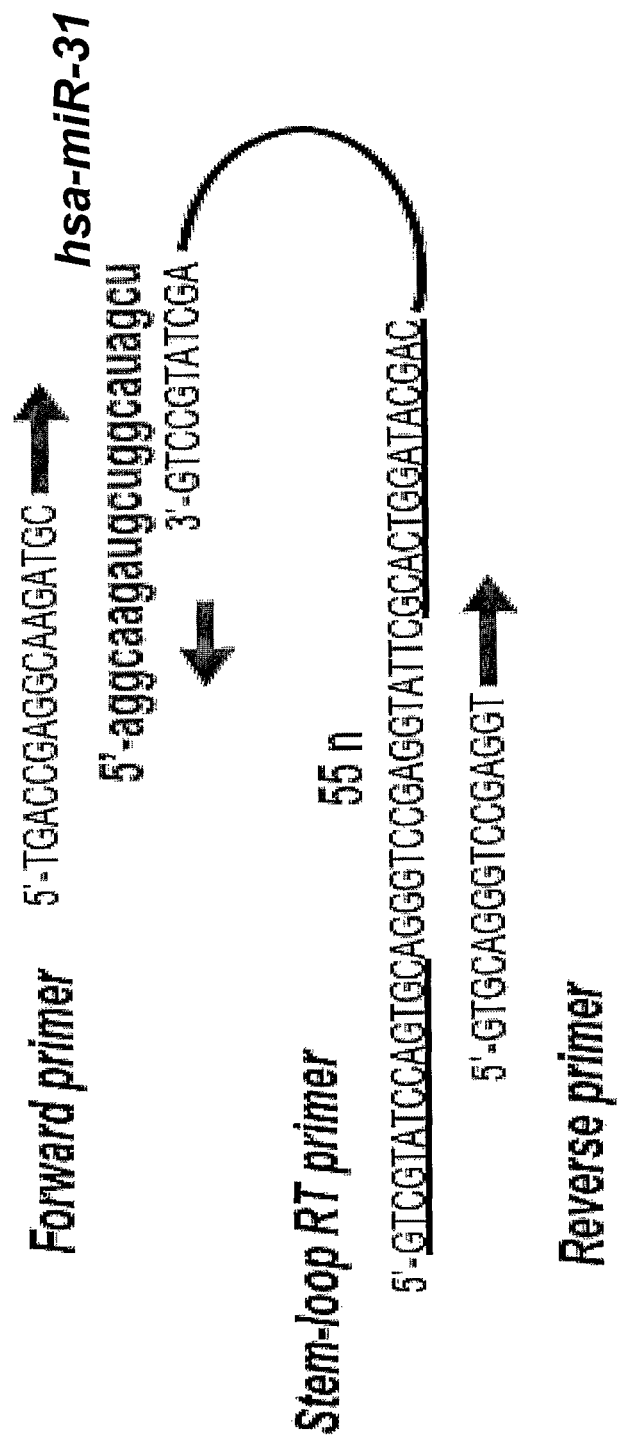
FIG. 1 shows looped RT-PCR on hsa-miR-31 (SEQ ID NO: 1). Stem-loop RT primer (SEQ ID NO: 4) was designed to anneal to mature miR-31 at its 3'-end and prime a 65-nucleotide RT product as shown. To ensure that only 3'-end is involved in the annealing, a hairpin was introduced in the stem-loop structure (underlined). During the PCR stage, forward (SEQ ID NO: 3) and reverse (SEQ ID NO: 5) primers were used to produce a 61-bp miR-31-specific PCR product.

The invention is based in part on the discovery that miRNA expression can serve as a novel tool for the treatment and diagnosis of mesothelioma and determination of prognosis of mesothelioma patients.

According to some aspects of the invention, specific nucleic acid sequences (SEQ ID NOS: 1-2), and sequences at least about 80% identical thereto, may be used for the treatment of mesothelioma. According to other aspects, specific nucleic acids (SEQ ID NOS: 1-2), and sequences at least about 80% identical thereto, may be used for the determination of prognosis of mesothelioma.

According to other aspects of the invention, the presence of a single microRNA has significant prognostic and treatment implications for malignant pleural mesothelioma. Analysis of microRNA expression may help identify cancer-associated miRs which are associated with the development of genetic and epigenetic changes critical for tumor initiation or progression.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9 and 7.0 are explicitly contemplated.

1. Definitions

About

As used herein, the term "about" refers to +/−10%.

Administering

"Administering" means providing a pharmaceutical agent or composition to a subject, and includes, but is not limited to, administering by a medical professional and self-administering.

"Pulmonary administration" means administration or delivery to the pulmonary epithelium or endothelium. Pulmonary delivery methods include, but are not limited to, aerosols, metered dose inhaler systems, powders (dry powder inhalers) and solutions (nebulizers), which may contain nanostructures such as micelles, liposomes, nanoparticles, and microemulsion delivery by aerosol and bronchoscopic instillation.

"Parenteral administration" means administration through injection or infusion. Parenteral administration includes, but is not limited to, subcutaneous administration, intravenous administration, or intramuscular administration.

"Subcutaneous administration" means administration just below the skin.

"Intravenous administration" means administration into a vein.

"Intratumoral administration" means administration within a tumor.

"Chemoembolization" means a procedure in which the blood supply to a tumor is blocked surgically or mechanically and chemotherapeutic agents are administered directly into the tumor.

"Intracavitary administration" means administration directly into a cavity with suspected or diagnosed tumor with said cavity represented as either left or right pleural cavity or the abdominal cavity or the pericardial space.

Amelioration

Amelioration as used herein, refers to a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

Antisense

The term "antisense," as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated.

Attached

"Attached" or "immobilized" as used herein refer to a probe and a solid support and may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe, or both. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

Biological Sample

"Biological sample" as used herein means a sample of biological tissue or fluid that comprises nucleic acids. Such samples include, but are not limited to, tissue or fluid isolated from subjects. Biological samples may also include sections of tissues such as biopsy and autopsy samples, FFPE samples, frozen sections taken for histological purposes, blood, plasma, serum, sputum, stool, tears, mucus, hair, and skin. Biological samples also include explants and primary and/or transformed cell cultures derived from animal or patient tissues.

Biological samples may also be blood, a blood fraction, urine, effusions, ascitic fluid, saliva, cerebrospinal fluid, cervical secretions, vaginal secretions, endometrial secretions, gastrointestinal secretions, bronchial secretions, sputum, cell line, tissue sample, cellular content of fine needle aspiration (FNA) or secretions from the breast. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

Cancer

The term "cancer" is meant to include all types of cancerous growths or oncogenic processes, metastatic tissues or malignantly transformed cells, tissues, or organs, irrespective of histopathologic type or stage of invasiveness. Examples of cancers include but are nor limited to solid tumors and leukemias, including: mesothelioma, glioblastoma, apudoma, choristoma, branchioma, malignant carcinoid syndrome, carcinoid heart disease, carcinoma (e.g., Walker, basal cell, basosquamous, Brown-Pearce, ductal, Ehrlich tumor, small cell lung, non-small cell lung (e.g., lung squamous cell carcinoma, lung adenocarcinoma and lung undifferentiated large cell carcinoma), oat cell, papillary, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymoma, mesonephroma, myo sarcoma, ameloblastoma, cementoma, odontoma, teratoma, thymoma, trophoblastic tumor, adeno-carcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma, phyllodes, fibrosarcoma, hemangiosarcoma, leimyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neurofibromatosis, and cervical dysplasia, and other conditions in which cells have become immortalized or transformed.

Cancer Prognosis

A forecast or prediction of the probable course or outcome of the cancer and response to its treatment. As used herein, cancer prognosis includes distinguishing between cancer stages and subtypes, and the forecast or prediction of any one or more of the following: duration of survival of a patient susceptible to or diagnosed with a cancer, duration of recurrence-free survival, time to disease relapse, duration of progression-free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer. As used herein, "prognostic for cancer" means providing a forecast or prediction of the probable course or outcome of the cancer. In some embodiments, "prognostic for cancer" comprises providing the forecast or prediction of (prognostic for) any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer.

Chemotherapeutic Agent

A drug used to treat a disease, especially cancer. In relation to cancer the drugs typically target rapidly dividing cells, such as cancer cells. Non-limiting examples of chemotherapeutic agents include cisplatin, carboplatin, camptothecins, doxorubicin, cyclophosphamide, paclitaxel, etoposide, vinblastine, Actinomycin D and cloposide.

Classification

"Classification" as used herein refers to a procedure and/or algorithm in which individual items are placed into groups or classes based on quantitative information on one or more characteristics inherent in the items (referred to as traits, variables, characters, features, etc) and based on a statistical model and/or a training set of previously labeled items. According to one embodiment, classification means determination of the type of cancer.

Complement

"Complement" or "complementary" as used herein means Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules. In some embodiments, the complementary sequence has a reverse orientation (5'-3').

Ct

Ct signals represent the first cycle of PCR where amplification crosses a threshold (cycle threshold) of fluorescence. Accordingly, low values of Ct represent high abundance or expression levels of the microRNA.

In some embodiments the PCR Ct signal is normalized such that the normalized Ct remains inversed from the expression level. In other embodiments the PCR Ct signal may be normalized and then inverted such that low normalized-inverted Ct represents low abundance or expression levels of the microRNA.

Detection

"Detection" means detecting the presence of a component in a sample. Detection also means detecting the absence of a component. Detection also means measuring the level of a component, either quantitatively or qualitatively. Detection also means identifying or diagnosing cancer in a subject. "Early detection" means identifying or diagnosing cancer in a subject at an early stage of the disease, especially before it causes symptoms.

Differential Expression

"Differential expression" means qualitative or quantitative differences in the temporal and/or cellular gene expression patterns within and among cells and tissue. Thus, a differentially expressed gene may qualitatively have its expression altered, including an activation or inactivation, in, e.g., normal or control versus disease tissue. Genes may be turned on or turned off in a particular state, relative to another state thus permitting comparison of two or more states. A qualitatively regulated gene may exhibit an expression pattern within a state or cell type which may be detectable by standard techniques. Some genes may be expressed in one state or cell type, but not in both. Alternatively, the difference in expression may be quantitative, e.g., in that expression is modulated, either up-regulated, resulting in an increased amount of transcript, or down-regulated, resulting in a decreased amount of transcript. The degree to which expression differs needs only be large enough to quantify via standard characterization techniques such as expression arrays, quantitative reverse transcriptase PCR, northern analysis, real-time PCR, in situ hybridization and RNase protection.

Dose

"Dose" as used herein means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

Dosage Unit

"Dosage unit" as used herein means a form in which a pharmaceutical agent is provided. In certain embodiments, a dosage unit is a vial containing lyophilized oligonucleotide. In certain embodiments, a dosage unit is a vial containing reconstituted oligonucleotide.

Expression Profile

"Expression profile" as used herein may mean a genomic expression profile, e.g., an expression profile of microRNAs. Profiles may be generated by any convenient means for determining a level of a nucleic acid sequence, e.g., quantitative hybridization of microRNA, labeled microRNA, amplified microRNA, cRNA, etc., quantitative PCR, ELISA for quantitation, and the like, and allow the analysis of differential gene expression between two samples. A subject or patient tumor sample, e.g., cells or collections thereof, e.g., tissues, is assayed. Samples are collected by any convenient method, as known in the art. Nucleic acid sequences of interest are nucleic acid sequences that are found to be predictive, including the nucleic acid sequences provided above, where the expression profile may include expression data for 5, 10, 20, 25, 50, 100 or more of, including all of the listed nucleic acid sequences. The term "expression profile" may also mean measuring the abundance of the nucleic acid sequences in the measured samples. In some embodiments, the term "expression profile" may be replaced by "expression level".

Expression Ratio

"Expression ratio" as used herein refers to relative expression levels of two or more nucleic acids as determined by detecting the relative expression levels of the corresponding nucleic acids in a biological sample.

FDR

When performing multiple statistical tests, for example in comparing the signal between two groups in multiple data features, there is an increasingly high probability of obtaining false positive results, by random differences between the groups that can reach levels that would otherwise be considered as statistically significant. In order to limit the proportion of such false discoveries, statistical significance is defined only for data features in which the differences reached a p-value (by two-sided t-test) below a threshold, which is dependent on the number of tests performed and the distribution of p-values obtained in these tests.

Fragment

"Fragment" is used herein to indicate a non-full length part of a nucleic acid or polypeptide. Thus, a fragment is itself also a nucleic acid or polypeptide, respectively.

Gene

"Gene" as used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

Groove Binder/Minor Groove Binder (MGB)

"Groove binder" and/or "minor groove binder" may be used interchangeably and refer to small molecules that fit into the minor groove of double-stranded DNA, typically in a sequence-specific manner. Minor groove binders may be long, flat molecules that can adopt a crescent-like shape and thus, fit snugly into the minor groove of a double helix, often displacing water. Minor groove binding molecules may typically comprise several aromatic rings connected by bonds with torsional freedom such as furan, benzene, or pyrrole rings. Minor groove binders may be antibiotics such as netropsin, distamycin, berenil, pentamidine and other aromatic diamidines, Hoechst 33258, SN 6999, aureolic antitumor drugs such as chromomycin and mithramycin, CC-1065, dihydrocyclopyrroloindole tripeptide ($DPI_3$), 1,2-dihydro-(3H)-pyrrolo[3,2-e]indole-7-carboxylate ($CDPI_3$), and related compounds and analogues, including those described in Nucleic Acids in Chemistry and Biology, 2d ed., Blackburn and Gait, eds., Oxford University Press, 1996, and PCT Published Application No. WO 03/078450, the contents of which are incorporated herein by reference. A minor groove binder may be a component of a primer, a probe, a hybridization tag complement, or combinations thereof.

Minor groove binders may increase the $T_m$ of the primer or a probe to which they are attached, allowing such primers or probes to effectively hybridize at higher temperatures.

Host Cell

"Host cell" as used herein may be a naturally occurring cell or a transformed cell that may contain a vector and may support replication of the vector.

Identity

"Identical" or "identity" as used herein in the context of two or more nucleic acids or polypeptide sequences mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

In Situ Detection

"In situ detection" as used herein means the detection of expression or expression levels in the original site hereby meaning in a tissue sample such as biopsy.

Inhibit

"Inhibit" as used herein may mean prevent, suppress, repress, reduce or eliminate.

Label

"Label" as used herein means a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

Logistic Regression

Logistic regression is part of a category of statistical models called generalized linear models. Logistic regression allows one to predict a discrete outcome, such as group membership, from a set of variables that may be continuous, discrete, dichotomous, or a mix of any of these. The dependent or response variable is dichotomous, for example, one of two possible types of cancer. Logistic regression models the natural log of the odds ratio, i.e. the ratio of the probability of belonging to the first group (P) over the probability of belonging to the second group (1-P), as a linear combination of the different expression levels (in log-space) and of other explaining variables. The logistic regression output can be used as a classifier by prescribing that a case or sample will be classified into the first type if P is greater than 0.5 or 50%. Alternatively, the calculated probability P can be used as a variable in other contexts such as a 1D or 2D threshold classifier.

1D/2D Threshold Classifier

"1D/2D threshold classifier" used herein may mean an algorithm for classifying a case or sample such as a cancer sample into one of two possible types such as two types of cancer or two types of prognosis (e.g., good and bad). For a 1D threshold classifier, the decision is based on one variable and one predetermined threshold value; the sample is assigned to one class if the variable exceeds the threshold and to the other class if the variable is less than the threshold. A 2D threshold classifier is an algorithm for classifying into one of two types based on the values of two variables. A score may be calculated as a function (usually a continuous function) of the two variables; the decision is then reached by comparing the score to the predetermined threshold, similar to the 1D threshold classifier.

Metastasis

"Metastasis" as used herein means the process by which cancer spreads from the place at which it first arose as a primary tumor to other locations in the body. The metastatic progression of a primary tumor reflects multiple stages, including dissociation from neighboring primary tumor cells, survival in the circulation, and growth in a secondary location.

Mismatch

"Mismatch" means a nucleobase of a first nucleic acid that is not capable of pairing with a nucleobase at a corresponding position of a second nucleic acid.

Modified Oligonucleotide

"Modified oligonucleotide" as used herein means an oligonucleotide having one or more modifications relative to a naturally occurring terminus, sugar, nucleobase, and/or internucleoside linkage. According to one embodiment, the modified oligonucleotide is a miRNA comprising a modification (e.g. labeled).

Modulation

"Modulation" as used herein means a perturbation of function or activity. In certain embodiments, modulation means an increase in gene expression. In certain embodiments, modulation means a decrease in gene expression.

Nucleic Acid

"Nucleic acid" or "oligonucleotide" or "polynucleotide", as used herein, mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single-stranded or double-stranded, or may contain portions of both double-stranded and single-stranded sequence. The nucleic acid may be DNA, both genomic and cDNA, RNA, or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e., ribonucleotides, containing a non-naturally occurring nucleobase instead of a naturally occurring nucleobase such as uridines or cytidines modified at the 5-position, e.g., 5-(2-amino) propyl uridine, 5-bromo uridine; adenosines and guanosines modified at the 8-position, e.g., 8-bromo guanosine; deaza nucleotides, e.g., 7-deaza-adenosine; O— and N— alkylated nucleotides, e.g., N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al. (Nature 438:685-689 (2005)) and Soutschek et al. (Nature 432:173-178 (2004)), which are incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver. Mixtures of naturally occurring nucleic acids and analogs may be made; alternatively, mixtures of different nucleic acid analogs, and mixtures of naturally occurring nucleic acids and analogs may be made.

Overall Survival Time

"Overall survival time" or "survival time", as used herein means the time period for which a subject survives after diagnosis of or treatment for a disease. In certain embodiments, the disease is cancer.

Pharmaceutical Agent

Pharmaceutical agent as used herein means a substance that provides a therapeutic effect when administered to a subject. "Pharmaceutical composition" means a mixture of substances suitable for administering to an individual that includes a pharmaceutical agent. For example, a pharmaceutical composition may comprise a modified oligonucleotide and a sterile aqueous solution. "Active pharmaceutical ingredient" means the substance in a pharmaceutical composition that provides a desired effect.

Prevention

Prevention as used herein means delaying or forestalling the onset or development or progression of a condition or disease for a period of time, including weeks, months, or years.

Progression-free Survival

"Progression-free survival" means the time period for which a subject having a disease survives, without the disease getting worse. In certain embodiments, progression-free survival is assessed by staging or scoring the disease. In certain embodiments, progression-free survival of a subject having cancer is assessed by evaluating tumor size, tumor number, and/or metastasis.

Probe

"Probe" as used herein means an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

Promoter

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents.

Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

Reduced Tumorigenicity

"Reduced tumorigenicity" as used herein refers to the conversion of hyperproliferative (e.g., neoplastic) cells to a less proliferative state. In the case of tumor cells, "reduced tumorigenicity" is intended to mean tumor cells that have become less tumorigenic or non-tumorigenic or non-tumor cells whose ability to convert into tumor cells is reduced or eliminated. Cells with reduced tumorigenicity either form no tumors in vivo or have an extended lag time of weeks to months before the appearance of in vivo tumor growth. Cells with reduced tumorigenicity may also result in slower growing three dimensional tumor mass compared to the same type of cells having fully inactivated or non-functional tumor suppressor gene growing in the same physiological milieu (e.g., tissue, organism age, organism sex, time in menstrual cycle, etc.).

Reference Expression Profile

As used herein the term "reference expression profile" means a value that statistically correlates to a particular outcome when compared to an assay result. In preferred embodiments the reference value is determined from statistical analysis of studies that compare microRNA expression with known clinical outcomes. The reference value may be a threshold score value or a cutoff score value. Typically a reference value will be a threshold above which one outcome is more probable and below which an alternative threshold is more probable.

Sensitivity

"sensitivity" used herein may mean a statistical measure of how well a binary classification test correctly identifies a condition, for example how frequently it correctly classifies a cancer into the correct type out of two possible types. The sensitivity for class A is the proportion of cases that are determined to belong to class "A" by the test out of the cases that are in class "A", as determined by some absolute or gold standard.

Side Effect

Side effect as used herein means a physiological response attributable to a treatment other than desired effects.

Selectable Marker

"Selectable marker" as used herein means any gene which confers a phenotype on a host cell in which it is expressed to facilitate the identification and/or selection of cells which are transfected or transformed with a genetic construct. Representative examples of selectable markers include the ampicillin-resistance gene ($Amp^r$), tetracycline-resistance gene ($Tc^r$), bacterial kanamycin-resistance gene ($Kan^r$) zeocin resistance gene, the AURI-C gene which confers resistance to the antibiotic aureobasidin A, phosphinothricin-resistance gene, neomycin phosphotransferase gene (nptII), hygromycin-resistance gene, beta-glucuronidase (GUS) gene, chloramphenicol acetyltransferase (CAT) gene, green fluorescent protein (GFP)-encoding gene and luciferase gene.

Specificity

"Specificity" used herein may mean a statistical measure of how well a binary classification test correctly identifies a condition, for example how frequently it correctly classifies a cancer into the correct type out of two possible types. The specificity for class A is the proportion of cases that are determined to belong to class "not A" by the test out of the cases that are in class "not A", as determined by some absolute or gold standard.

Stringent Hybridization Conditions

"Stringent hybridization conditions" as used herein mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium).

Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

Substantially Complementary

"Substantially complementary" as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

Substantially Identical

"Substantially identical" as used herein means that a first and a second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

Subject

As used herein, the term "subject" refers to a human or non-human animal selected for treatment or therapy. The methods of the present invention are preferably applied to human subjects. "Subject in need thereof" refers to a subject identified as in need of a therapy or treatment. In certain embodiments, a subject is in need of treatment for mesothelioma. In such embodiments, a subject has one or more clinical indications of mesothelioma or is at risk for developing mesothelioma.

Target Nucleic Acid

"Target nucleic acid" as used herein means a nucleic acid or variant thereof that may be bound by another nucleic acid. A target nucleic acid may be a DNA sequence. The target nucleic acid may be RNA. The target nucleic acid may comprise a mRNA, tRNA, shRNA, siRNA or Piwi-interacting RNA, or a pri-miRNA, pre-miRNA, miRNA, or anti-miRNA.

The target nucleic acid may comprise a target miRNA binding site or a variant thereof. One or more probes may bind the target nucleic acid. The target binding site may comprise 5-100 or 10-60 nucleotides. The target binding site may comprise a total of 5, 6, 7, 8, 9, 10, 11, 12, 13, 14, 15, 16, 17, 18, 19, 20, 21, 22, 23, 24, 25, 26, 27, 28, 29, 30-40, 40-50, 50-60, 61, 62 or 63 nucleotides. The target site sequence may comprise at least 5 nucleotides of the sequence of a target miRNA binding site disclosed in WO2006/092738, U.S. patent application Ser. Nos. 11/418,718 or 11/429,720, the contents of which are incorporated herein.

Therapy

"Therapy" as used herein means a disease treatment method. In certain embodiments, therapy includes, but is not limited to, tyrosine kinase inhibition therapy, chemotherapy, surgical resection, transplant, radiation therapy, "gene therapy", immunotherapy, and/or chemoembolization. "Therapeutic agent" means a pharmaceutical agent used for the cure, amelioration or prevention of a disease. "Recommended therapy" means a treatment recommended by a medical professional for the treatment, amelioration, or prevention of a disease.

Therapeutically Effective Amount

"Therapeutically effective amount" or "therapeutically efficient", used herein as to a drug dosage, refer to dosage that provides the specific pharmacological response for which the drug is administered in a significant number of subjects in need of such treatment. The "therapeutically effective amount" may vary according to, for example, the physical condition of the patient, the age of the patient and the severity of the disease.

Threshold Expression Level

As used herein, the phrase "threshold expression level" refers to a reference expression value. Measured values are compared to a corresponding threshold expression level to determine the prognosis of a subject.

Tissue Sample

As used herein, a tissue sample is tissue obtained from a tissue biopsy using methods well known to those of ordinary skill in the related medical arts. The phrase "suspected of being cancerous" as used herein means a cancer tissue sample believed by one of ordinary skill in the medical arts to contain cancerous cells. Methods for obtaining the sample from the biopsy include gross apportioning of a mass, microdissection, laser-based microdissection, or other art-known cell-separation methods.

Treat

"Treat" or "treating" used herein when referring to protection of a subject from a condition may mean preventing, suppressing, repressing, or eliminating the condition. Preventing the condition involves administering a composition described herein to a subject prior to onset of the condition. Suppressing the condition involves administering the composition to a subject after induction of the condition but before its clinical appearance. Repressing the condition involves administering the composition to a subject after clinical appearance of the condition such that the condition is reduced or prevented from worsening. Elimination of the condition involves administering the composition to a subject after clinical appearance of the condition such that the subject no longer suffers from the condition.

Tumor Suppressor Protein

"Tumor suppressor protein", as used herein, may refer to a protein that suppresses tumorigenesis. Tumor suppressor proteins generally function as negative regulators of cell cycle progression or cell proliferation. Tumor suppressor proteins may, in some embodiments, act to enforce cell cycle arrest in response to specific signals, such as DNA damage, thereby allowing DNA repair to occur prior to DNA replication. In other embodiments, tumor suppressors may act to induce programmed cell death (apoptosis) in response to specific developmental signals or under circumstances where DNA repair cannot be completed. As used herein, a tumor suppressor protein may be, but is not limited to, cyclin-dependent kinase inhibitor 2A (CDKN2A) or 2B (CDKN2B). These genes prevent the activation of the CDK kinases and are located in a region that is frequently mutated and deleted in a wide variety of tumors.

Unit Dosage Form

"Unit dosage form", used herein, may refer to a physically discrete unit suitable as a unitary dosage for a human or animal subject. Each unit may contain a predetermined quantity of a composition described herein, calculated in an amount sufficient to produce a desired effect in association with a pharmaceutically acceptable diluent, carrier or vehicle. The specifications for a unit dosage form may depend on the particular composition employed and the effect to be achieved, and the pharmacodynamics associated with the composition in the host.

Variant

"Variant" as used herein referring to a nucleic acid means (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

Vector

"Vector" as used herein means a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

Wild Type

As used herein, the term "wild-type" sequence refers to a coding, a non-coding or an interface sequence which is an allelic form of sequence that performs the natural or normal function for that sequence. Wild-type sequences include multiple allelic forms of a cognate sequence, for example, multiple alleles of a wild-type sequence may encode silent or conservative changes to the protein sequence that a coding sequence encodes.

2. MicroRNAs and their Processing

A gene coding for a microRNA (miRNA) may be transcribed leading to production of an miRNA precursor known as the pri-miRNA. The pri-miRNA may be part of a polycistronic RNA comprising multiple pri-miRNAs. The pri-miRNA may form a hairpin structure with a stem and loop. The stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 60-70 nucleotide precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of the stem (~10 nucleotides) extending beyond the Drosha cleavage site may be essential for efficient processing. The pre-miRNA may then be actively transported from the nucleus to the cytoplasm by Ran-GTP and the export receptor Exportin-5.

The pre-miRNA may be recognized by Dicer, which is also an RNase III endonuclease. Dicer may recognize the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repression or activation), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-7 of the miRNA. Only one case has been reported in animals where the interaction between the miRNA and its target was along the entire length of the miRNA. This was shown for miR-196 and Hox B8 and it was further shown that miR-196 mediates the cleavage of the Hox B8 mRNA (Yekta et al., Science 2004; 304:594-596). Otherwise, such interactions are known only in plants (Bartel & Bartel, Plant Physiol 2003; 132:709-717).

A number of studies have studied the base-pairing requirement between miRNA and its mRNA target for achieving efficient inhibition of translation (reviewed by Bartel, Cell 2004; 116:281-297). In mammalian cells, the first eight nucleotides of the miRNA may be important (Doench & Sharp, GenesDev 2004; 18:504-511). However, other parts of the microRNA may also participate in mRNA binding. Moreover, sufficient base pairing at the 3' can compensate for insufficient pairing at the 5' (Brennecke et al., PLoS Biol 2005; 3:e85).

Computation studies, analyzing miRNA binding on whole genomes have suggested a specific role for bases 2-7 at the 5' of the miRNA in target binding but the role of the first nucleotide, found usually to be "A" was also recognized (Lewis et al., Cell 2005; 120:15-20). Similarly, nucleotides 1-7 or 2-8 were used by Krek et al. (Nat Genet 2005; 37:495-500) to identify and validate targets.

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to down-regulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and the binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

3. Nucleic Acids

Nucleic acids are provided herein. The nucleic acids comprise the sequence of SEQ ID NO: 1-30, or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559, which is incorporated by reference.

3a. Nucleic Acid Complexes

The nucleic acid may further comprise one or more of the following: a peptide, a protein, a RNA-DNA hybrid, an antibody, an antibody fragment, a Fab fragment, and an aptamer.

3b. Pri-miRNA

The nucleic acid may comprise a sequence of a pri-miRNA or a variant thereof. The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof.

The pri-miRNA may form a hairpin structure. The hairpin may comprise a first and a second nucleic acid sequence that are substantially complimentary. The first and second nucleic acid sequence may be from 37-50 nucleotides. The first and second nucleic acid sequence may be separated by a third sequence of from 8-12 nucleotides. The hairpin structure may have a free energy of less than −25 Kcal/mole, as calculated by the Vienna algorithm, with default parameters as described in Hofacker et al. (Monatshefte f. Chemie 1994; 125:167-188), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides. The sequence of the pri-miRNA may comprise the sequence of SEQ ID NOS: 1-2, or variants thereof.

3c. Pre-miRNA

The nucleic acid may also comprise a sequence of a pre-miRNA or a variant thereof. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-2, or variants thereof.

3d. miRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of SEQ ID NO: 1, or variants thereof.

3e. Anti-miRNA

The nucleic acid may also comprise a sequence of an anti-miRNA capable of blocking the activity of a miRNA or miRNA*, such as by binding to the pri-miRNA, pre-miRNA, miRNA or miRNA* (e.g., antisense or RNA silencing), or by binding to the target binding site. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the anti-miRNA may comprise (a) at least 5 nucleotides that are substantially identical or complimentary to the 5' of a miRNA and at least 5-12 nucleotides that are substantially complimentary to the flanking regions of the target site from the 5' end of the miRNA, or (b) at least 5-12 nucleotides that are substantially identical or complimentary to the 3' of a miRNA and at least 5 nucleotide that are substantially complimentary to the flanking region of the target site from the 3' end of the miRNA. The sequence of the anti-miRNA may comprise the complement of SEQ ID NOS: 1-2, or variants thereof.

3f. microRNA Binding Site of Target

The nucleic acid may also comprise a sequence of a target binding site or a variant thereof. The target site sequence may comprise a total of 5-100 or 10-60 nucleotides. The target site sequence may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62 or 63 nucleotides. The binding sites may comprise the sequence of SEQ ID NOS: 28-30, or variants thereof.

4. Synthetic Gene

A synthetic gene is also provided comprising a nucleic acid described herein operably linked to a transcriptional and/or translational regulatory sequence. The synthetic gene may be capable of modifying the expression of a target gene with a binding site for a nucleic acid described herein. Expression of the target gene may be modified in a cell, tissue or organ. The synthetic gene may be synthesized or derived from naturally-occurring genes by standard recombinant techniques. The synthetic gene may also comprise terminators at the 3'-end of the transcriptional unit of the synthetic gene sequence. The synthetic gene may also comprise a selectable marker.

5. Vector

A vector is also provided comprising a synthetic gene described herein. The vector may be an expression vector. An expression vector may comprise additional elements. For example, the expression vector may have two replication systems allowing it to be maintained in two organisms, e.g., in one host cell for expression and in a second host cell (e.g., bacteria) for cloning and amplification. For integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. The vector may also comprise a selectable marker gene to allow the selection of transformed host cells.

6. Host Cell

A host cell is also provided comprising a vector, synthetic gene or nucleic acid described herein. The cell may be a bacterial, fungal, plant, insect or animal cell. For example, the host cell line may be DG44 and DUXB11 (Chinese Hamster Ovary lines, DHFR minus), HeLa (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3×63-Ag3.653 (mouse myeloma), BFA-1c1BPT (bovine endothelial cells), RAH (human lymphocyte) and 293 (human kidney). In one embodiment, host cell lines may be available from commercial services, the American Tissue Culture Collection or from published literature. In another embodiment, host cell lines may also be produced from surgical specimens derived from patients.

7. Probes

A probe is provided herein. A probe may comprise a nucleic acid. The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may comprise a nucleic acid of 18-25 nucleotides.

A probe may be capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. A probe may be single stranded or partially single and partially double stranded. The strandedness of the probe is dictated by the structure, composition, and properties of the target sequence. Probes may be directly labeled or indirectly labeled.

The probe may be a test probe. The test probe may comprise a nucleic acid sequence that is complementary to a miRNA, a miRNA*, a pre-miRNA, or a pri-miRNA.

The probe may further comprise a linker. The linker may be 10-60 nucleotides in length. The linker may be 20-27 nucleotides in length. The linker may be of sufficient length to allow the probe to be a total length of 45-60 nucleotides. The linker may not be capable of forming a stable secondary structure, or may not be capable of folding on itself, or may not be capable of folding on a non-linker portion of a nucleic acid contained in the probe. The sequence of the linker may not appear in the genome of the animal from which the probe non-linker nucleic acid is derived.

The sequence of the probe may be selected from sequences complementary to SEQ ID NOS: 1-2 and sequences at least about 80% identical thereto.

8. Reverse Transcription

Target sequences of a cDNA may be generated by reverse transcription of the target RNA. Methods for generating cDNA may be reverse transcribing polyadenylated RNA or alternatively, RNA with a ligated adaptor sequence.

The RNA may be ligated to an adapter sequence prior to reverse transcription. A ligation reaction may be performed by T4 RNA ligase to ligate an adaptor sequence at the 3' end of the RNA. Reverse transcription (RT) reaction may then be performed using a primer comprising a sequence that is complementary to the 3' end of the adaptor sequence.

Polyadenylated RNA may be used in a reverse transcription (RT) reaction using a poly (T) primer comprising a 5' adaptor sequence. The poly(T) sequence may comprise 8, 9, 10, 11, 12, 13, or 14 consecutive thymines.

In another method, a reverse primer may be used to produce a chimeric cDNA product. In this method, a stem-loop reverse transcriptase primer is designed to anneal to a selected RNA sequence. To ensure that only the 3' end is involved in annealing, a hairpin is introduced into the stem-loop structure. The sequence of the stem-loop RT primer may comprise SEQ ID NO: 4, or sequences at least about 80% identical thereto.

The reverse transcript of the RNA may be amplified by real-time PCR, using a specific forward primer comprising at least 15 nucleic acids complementary to the target nucleic acid and a 5' tail sequence; a reverse primer that is complementary to the 3' end of the adaptor sequence; and a probe comprising at least 8 nucleic acids complementary to the target nucleic acid. The probe may be partially complementary to the 5' end of the adaptor sequence. The sequence of the probe may be selected from sequences complementary to SEQ ID NOS: 1-2 and sequences at least about 80% identical thereto. The sequence of the forward primer may comprise SEQ ID NO: 3, or sequences at least about 80% identical thereto. The sequence of the reverse primer may comprise SEQ ID NO: 5, or sequences at least about 80% identical thereto.

Methods of amplifying target nucleic acids are described herein. The amplification may be by a method comprising PCR. The first cycles of the PCR reaction may have an annealing temp of 56° C., 57° C., 58° C., 59° C., or 60° C. The first cycles may comprise 1-10 cycles. The remaining cycles of the PCR reaction may be 60° C. The remaining cycles may comprise 2-40 cycles. The annealing temperature may cause the PCR to be more sensitive. The PCR may generate longer products that can serve as higher stringency PCR templates.

The PCR reaction may comprise a forward primer. The forward primer may comprise 15, 16, 17, 18, 19, 20, or 21 nucleotides identical to the target nucleic acid.

The 3' end of the forward primer may be sensitive to differences in sequence between a target nucleic acid and a sibling nucleic acid.

The forward primer may also comprise a 5' overhanging tail. The 5' tail may increase the melting temperature of the forward primer. The sequence of the 5' tail may comprise a sequence that is non-identical to the genome of the animal from which the target nucleic acid is isolated. The sequence of the 5' tail may also be synthetic. The 5' tail may comprise 8, 9, 10, 11, 12, 13, 14, 15, or 16 nucleotides.

The PCR reaction may comprise a reverse primer. The reverse primer may be complementary to a target nucleic acid. The reverse primer may also comprise a sequence complementary to an adaptor sequence. The sequence complementary to an adaptor sequence may comprise 12-24 nucleotides.

9. Biochip

A biochip is also provided. The biochip may comprise a solid substrate comprising an attached probe or plurality of probes described herein. The probes may be capable of hybridizing to a target sequence under stringent hybridization conditions. The probes may be attached at spatially defined locations on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrate materials include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The substrate of the biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker.

The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

10. Diagnostics

A method of diagnosis is also provided. The method comprises detecting a differential expression level of mesothelioma-associated nucleic acids in a biological sample. The sample may be derived from a patient. Diagnosis of a cancer state, and its histological type, in a patient may allow for prognosis and selection of therapeutic strategy. Further, the developmental stage of cells may be classified by determining temporarily expressed cancer-associated nucleic acids.

In situ hybridization of labeled probes to tissue arrays may be performed. When comparing the fingerprints between an individual and a standard, the skilled artisan can make a diagnosis, a prognosis, or a prediction based on the findings. It is further understood that the genes that indicate the diagnosis may differ from those which indicate the prognosis and molecular profiling of the condition of the cells may lead to distinctions between responsive or refractory conditions or may be predictive of outcomes.

11. Kits

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein.

For example, the kit may be used for the amplification, detection, identification or quantification of a target nucleic acid sequence. The kit may comprise a poly(T) primer, a forward primer, a reverse primer, and a probe.

Any of the compositions described herein may be comprised in a kit. In a non-limiting example, reagents for isolating miRNA, labeling miRNA, and/or evaluating a miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, components for in situ hybridization and components for isolating miRNA. Other kits of the invention may include components for making a nucleic acid array comprising miRNA, and thus, may include, for example, a solid support.

12. Compositions

A pharmaceutical composition is also provided. The composition may comprise a nucleic acid described herein and optionally a pharmaceutically acceptable carrier. The composition may encompass modified oligonucleotides that are identical, substantially identical, substantially complementary or complementary to any nucleobase sequence version of the miRNAs described herein or a precursor thereof.

In certain embodiments, a nucleobase sequence of a modified oligonucleotide is fully identical or complementary to a miRNA nucleobase sequence listed herein, or a precursor thereof. In certain embodiments, a modified oligonucleotide has a nucleobase sequence having one mismatch with respect to the nucleobase sequence of the mature miRNA, or a precursor thereof. In certain embodiments, a modified oligonucleotide has a nucleobase sequence having two mismatches with respect to the nucleobase sequence of the miRNA, or a precursor thereof. In certain such embodiments, a modified oligonucleotide has a nucleobase sequence having no more than two mismatches with respect to the nucleobase sequence of the mature miRNA, or a precursor thereof. In certain such embodiments, the mismatched nucleobases are contiguous. In certain such embodiments, the mismatched nucleobases are not contiguous.

In certain embodiments, a modified oligonucleotide consists of a number of linked nucleosides that is equal to the length of the mature miRNA.

In certain embodiments, the number of linked nucleosides of a modified oligonucleotide is less than the length of the mature miRNA. In certain such embodiments, the number of linked nucleosides of a modified oligonucleotide is one less than the length of the mature miRNA. In certain such embodiments, a modified oligonucleotide has one less nucleoside at the 5' terminus. In certain such embodiments, a modified oligonucleotide has one less nucleoside at the 3' terminus. In certain such embodiments, a modified oligonucleotide has two fewer nucleosides at the 5' terminus. In certain such embodiments, a modified oligonucleotide has two fewer nucleosides at the 3' terminus. A modified oligonucleotide having a number of linked nucleosides that is less than the length of the miRNA, wherein each nucleobase of a modified oligonucleotide is complementary to each nucleobase at a corresponding position in a miRNA, is considered to be a modified oligonucleotide having a nucleobase sequence that is fully complementary to a portion of a miRNA sequence.

In certain embodiments, a modified oligonucleotide consists of 15 to 30 linked nucleosides. In certain embodiments, a modified oligonucleotide consists of 19 to 24 linked nucleosides. In certain embodiments, a modified oligonucleotide consists of 21 to 24 linked nucleosides. In certain embodiments, a modified oligonucleotide consists of 15 linked nucleosides. In certain embodiments, a modified oligonucleotide consists of 16 linked nucleosides. In certain embodiments, a modified oligonucleotide consists of 17 linked nucleosides. In certain embodiments, a modified oligonucleotide consists of 18 linked nucleosides. In certain embodiments, a modified oligonucleotide consists of 19 linked nucleosides. In certain embodiments, a modified oligonucleotide consists of 20 linked nucleosides. In certain embodiments, a modified oligonucleotide consists of 21 linked nucleosides. In certain embodiments, a modified oligonucleotide consists of 22 linked nucleosides. In certain embodiments, a modified oligonucleotide consists of 23 linked nucleosides. In certain embodiments, a modified oligonucleotide consists of 24 linked nucleosides. In certain embodiments, a modified oligonucleotide consists of 25 linked nucleosides. In certain embodiments, a modified oligonucleotide consists of 26 linked nucleosides. In certain embodiments, a modified oligonucleotide consists of 27 linked nucleosides. In certain embodiments, a modified oligonucleotide consists of 28 linked nucleosides. In certain embodiments, a modified oligonucleotide consists of 29 linked nucleosides. In certain embodiments, a modified oligonucleotide consists of 30 linked nucleosides.

Modified oligonucleotides of the present invention may comprise one or more modifications to a nucleobase, sugar, and/or internucleoside linkage. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, a modified oligonucleotide of the present invention comprises one or more modified nucleosides. In certain such embodiments, a modified nucleoside is a stabilizing nucleoside. An example of a stabilizing nucleoside is a sugar-modified nucleoside.

In certain embodiments, a modified nucleoside is a sugar-modified nucleoside. In certain such embodiments, the sugar-modified nucleosides can further comprise a natural or modified heterocyclic base moiety and/or a natural or modified internucleoside linkage and may include further modifications independent from the sugar modification. In certain embodiments, a sugar modified nucleoside is a 2'-modified nucleoside, wherein the sugar ring is modified at the 2' carbon from natural ribose or 2'-deoxy-ribose. In certain embodiments, 2'-O-methyl group is present in the sugar residue.

The modified oligonucleotides designed according to the teachings of the present invention can be generated according to any oligonucleotide synthesis method known in the art, including both enzymatic syntheses or solid-phase syntheses. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology", Volumes I-III, John Wiley & Sons, Baltimore, Md.; Perbal, B. (1988), "A Practical Guide to Molecular Cloning", John Wiley & Sons, New York; and Gait, M. J., ed. (1984), "Oligonucleotide Synthesis"; utilizing solid-phase chemistry, e.g., cyanoethyl phosphoramidite followed by deprotection, desalting, and purification by, for example, an automated trityl-on method or HPLC.

It will be appreciated that an oligonucleotide comprising an RNA molecule can be also generated using an expression vector as described herein.

The compositions may be used for therapeutic applications. The pharmaceutical composition may be administered by known methods, including wherein a nucleic acid is introduced into a desired target cell in vitro or in vivo.

Methods for the delivery of nucleic acid molecules are described in Akhtar et al., (Trends Cell Bio. 1992; 2:139-144). WO 94/02595 describes general methods for delivery of RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form) and/or intrathecal delivery (Gold, Neuroscience 1997; 76:1153-1158). Other approaches include the use of various transport and carrier systems, for example, through the use of conjugates and biodegradable polymers. More detailed descriptions of nucleic acid delivery and administration are provided for example in WO93/23569, WO99/05094, and WO99/04819.

The nucleic acids can be introduced into tissues or host cells by any number of routes, including viral infection, microinjection, or fusion of vesicles. Jet injection may also be used for intra-muscular administration, as described by Furth et al. (Anal Biochem 1992; 205:365-368, 1992). The nucleic acids can be coated onto gold microparticles, and delivered intradermally by a particle bombardment device, or "gene gun" as described in the literature (see, for example, Tang et al. Nature 1992; 356:152-154), where gold microprojectiles are coated with the DNA, then bombarded into skin cells.

13. Treatments

A method of treatment is also provided. A subject may be diagnosed with mesothelioma following the administration of medical tests well-known to those in the medical profession. In certain embodiments, the present invention provides methods for the treatment of mesothelioma comprising administering to a subject in need thereof a pharmaceutical composition. Administration of a pharmaceutical composition of the present invention to a subject having mesothelioma may result in one or more clinically desirable outcomes. Such clinically desirable outcomes include reduction of tumor number or reduction of tumor size. Additional clinically desirable outcomes include the extension of overall survival time of the subject, and/or extension of progression-free survival time of the subject. In certain embodiments, administration of a pharmaceutical composition of the invention prevents an increase in tumor size and/or tumor number. In certain embodiments, administration of a pharmaceutical composition of the invention prevents the recurrence of tumors. Administration of a pharmaceutical composition of the present invention results in desirable phenotypic effects. A subject's response to treatment may be evaluated by tests similar to those used to diagnosis the mesothelioma. Response to treatment may also be assessed by measuring biomarkers in blood, for comparison to pre-treatment levels of biomarkers.

The compounds provided herein maybe useful for the treatment of mesothelioma.

Tumor treatments often comprise more than one therapy. As such, in certain embodiments the present invention provides methods for treating mesothelioma comprising administering to a subject in need thereof a pharmaceutical composition of the present invention, and further comprising administering at least one additional therapy.

In certain embodiments, an additional therapy may also be designed to treat mesothelioma. An additional therapy may be a chemotherapeutic agent. In some embodiments, the chemotherapeutic agent may be, but is not limited to, cisplatin, pemetrexed, navelbine, gemcitabine, carboplatin, camptothecins, doxorubicin, cyclophosphamide, etoposide, vinblastine, Actinomycin D and cloposide. In some embodiments, an additional therapy may be a small molecule or antibody, which may, in some embodiments, interfere with a receptor, or other molecule involved in necessary survival, proliferation, or invasion pathways in the disease. In some embodiments, the small molecule or antibody may be, but is not limited to, vorinostat, a PI3 kinase inhibitor, a mTOR inhibitor, a proteosome inhibitor, a vascular targeting agent, or an angiogenesis inhibitor. In some embodiments, an additional therapy may be the use of radiation.

In certain embodiments, an additional therapy may be a pharmaceutical agent that enhances the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines, e.g., the immunostimulating complex (ISCOM), which comprises a vaccine formulation that combines a multimeric presentation of antigen and an adjuvant.

In certain such embodiments, the additional therapy is selected to treat or ameliorate a side effect of one or more pharmaceutical compositions of the present invention. Such side effects include, without limitation, injection site reactions, liver function test abnormalities, renal function abnormalities, liver toxicity, renal toxicity and central nervous system abnormalities.

In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

In certain embodiments, suitable administration routes of a pharmaceutical composition for the treatment of mesothelioma include, but are not limited to, oral, buccal, intradermal, transdermal, rectal, transmucosal, intestinal, enteral, topical, suppository, through inhalation, intratracheal, intrathecal, intraventricular, intraperitoneal, intrapleural, intrapericardial, intranasal, intraocular, intratumoral, and parenteral (e.g., intravenous, intramuscular, intramedullary, and subcutaneous). An additional suitable administration route includes chemoembolization. In certain embodiments, pharmaceutical intrathecals are administered to achieve local rather than systemic exposures. For example, pharmaceutical compositions may be injected directly in the area of desired effect (e.g., into a tumor).

In certain embodiments, a pharmaceutical composition of the present invention is administered in the form of a dosage unit (e.g., tablet, capsule, bolus, etc.). In certain embodiments, such pharmaceutical compositions comprise a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the present invention comprises a dose selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, the compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like, which do not deleteriously interact with the formulation.

In certain embodiments, pharmaceutical compositions of the present invention comprise one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulosem and polyvinylpyrrolidone.

In certain embodiments, a pharmaceutical composition of the present invention is prepared using known techniques, including, but not limited to mixing, dissolving, granulating, dragee-making, levigating, emulsifying, encapsulating, entrapping or tabletting processes.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition of the present invention is a solid (e.g., a powder, granule, tablet, and/or capsule). In certain of such embodiments, a solid pharmaceutical composition is prepared using ingredients known in the art, including, but not limited to, starches, sugars, diluents, granulating agents, lubricants, binders, and disintegrating agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition of the present invention is prepared for oral administration. In certain of such embodiments, a pharmaceutical composition is formulated by combining one or more compounds with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, the therapeutically effective amount of the pharmaceutical composition of the present invention is sufficient to prevent, alleviate or ameliorate symptoms of a disease or to prolong the survival of the subject being treated. Determination of a therapeutically effective amount is well within the capability of those skilled in the art.

In certain embodiments, the pharmaceutical composition of the present invention is formulated as a prodrug. In certain embodiments, upon in vivo administration, a prodrug is chemically converted to the biologically, pharmaceutically or therapeutically more active form of the composition. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

The following examples are presented in order to more fully illustrate some embodiments of the invention. They should, in no way be construed, however, as limiting the broad scope of the invention.

EXAMPLES

Materials and methods
1.1 Cell Lines

Mesothelioma cell lines HP1, HP3, H2373, H2452, H2591, H2595, H2596, and H2461 were produced from patients with surgically resected malignant mesothelioma. Tert-immortalized mesothelial cells LP9, primary mesothelial cell culture NYU-590.2 (passage 3), and SV40-transformed mesothelial cells Met5A were used as benign controls.

1.2 RNA Isolation and miR Microarray Analysis

MicroRNA-containing RNA was isolated from near-confluent cells using mirVana kit (Ambion) and assessed for integrity in agarose gels. Custom miR arrays were prepared as described previously. Briefly, 903 DNA oligonucleotide probes representing miRNAs were spotted in triplicate on coated microarray slides (Nexterion® Slide E, Schott, Mainz, Germany). Total RNA (3-5 μg) was labeled by ligation of an RNA-linker, p-rCrU-Cy/dye (Cy3 or Cy5) to the 3'-end. Slides were incubated with the labeled RNA for 12-16 h at 42° C. and then washed twice. Arrays were scanned at a resolution of 10 μm, and images were analyzed using SpotReader software (Niles Scientific, Portola Valley, Calif.). Microarray spots were combined and signals normalized.

1.3 Microarray Data Analysis and Statistics

Expressions of all miRNAs were normalized. Each comparison was between two groups. Only miRNAs which had a median signal higher than signal background levels (normalized fluorescence signal of ~300) in at least one of the two groups were tested. Expression levels between each two groups of samples were compared using the two-sided Student t-test. To correct for multiple hypothesis testing the Benjamin-Hochberg false detection rate (FDR) method was used, with FDR=0.1. Any miRNA which had a p-value below the FDR-moderated threshold was taken to be significantly differentially expressed A miRNA was, however, only considered truly differential if the fold-change between group medians was at least 5.

1.4 Introduction of miR-31 Mimic and Inhibitor in Malignant Mesothelioma Cells mRNA mimic (miR-31), miR-31 inhibitor and negative oligonucleotide control were purchased from Ambion (Austin, Tex.). For transfection of these oligonucleotides, malignant mesothelioma cells were plated at 60-70% confluency in 10-cm dishes. Lipofectamine-2000 and the protocol recommended by Invitrogen (Carlsbad, Calif.) were used, with 40 nmoles of miR-31 mimic or negative control and with 80 mmoles of miR-31 inhibitor added to 15 ml of media. Transfection medium was removed after 4 hours of incubation and replaced with fresh DMEM/10% FBS medium. MiR-31-transfected cells were trypsinized 48 h post-transfection, counted and assayed for proliferation, colony formation in soft agar, wound closure and matrigel invasion in triplicate experiments.

1.5 Cell Cycle Analysis

Cell cycle analysis was performed in triplicates on permeabilized cells using a routine propidium-iodide staining protocol. Cells plated at ~25-30% confluency were transfected with miR mimic or inhibitor as described above and grown for 48 hours until ~80% confluency was reached. Trypsinized cells were then washed with PBS and fixed with cold 70% ethanol. RNAse treatment (0.2 mg/ml) of PBS pre-washed cells was performed for 30 min at 37° C. At the last stage, cells were stained with 50 μg/ml propidium iodide (Invitrogen, Carlsbad, Calif.) and assessed for cell cycle using Becton Dickinson FACScalibur system (Franklin Lakes, N.J.) and Modfit LT 3.0 software.

1.6 RT-PCR Validation of miR-31 Expression

RT-PCR validation was performed using an end-point modification of the looped RT-PCR technology. In the first stage, a reverse primer to miR-31 and Superscript II Reverse Transcriptase kit (Invitrogen, Carlsbad, Calif.) were used to produce a chimeric cDNA product on miR-31 (FIG. 1). Modifications introduced by Varkonyi-Gasic et al. (Plant Methods 2007; 3:12) were used to increase efficiency of reverse transcription and PCR. The product of looped RT-PCR was analyzed in 4% Metaphor agarose (Lonza, Rockland, Me.).

1.7 Genome-Wide Expression Profiling of miR-31-Affected Genes

Genome-wide expression profiling of miR-31-affected genes was performed using Genechip system. The RNA quality and quantity was determined using Agilent 2100 Bioanalyzer and Nanodrop ND-1000. Total RNA (100 ng) was used to prepare cRNA following the Affymetrix 3'IVT Express Kit labeling protocol and standardized array processing procedures recommended by Affymetrix, including hybridization, fluidics processing and scanning of the Affymetrix HG-U133 Plus 2.0 arrays. The raw data (Affymetrix CEL files) were normalized using Robust Multichip Average algorithm (RMA) (Irizarry et al., Nucleic Acids Res 2003; 31:e15) in GeneSpring GX software (Agilent Technologies, Santa Clara, Calif.). Gene Ontology analysis of differentially expressed genes was performed using GeneCodis portal (Carmona-Saez, P et al., 2007; Genome Biol 8:R3; Nogales-Cadenas, R et al., 2009; Nucleic Acids Res 37:W317-322).

1.8 Validation of Putative miR-31 Targets

Validation of putative miR-31 targets was performed using our U133 Plus 2.0 Affymetrix expression array data from 32 malignant mesothelioma and 7 normal peritonea specimens as described by Ivanov, S V et al. (Int J Cancer, 124:589-599, 2009) and Ivanova, A V et al. (Clin Cancer Res, 15:2602-2611, 2009).

1.9 RT-PCR Validation of Gene Expression on Clinical Malignant Mesothelioma Specimens RT-PCR validation of gene expression on clinical malignant mesothelioma specimens was performed using SingleTube Superscript II kit (Invitrogen, Carlsbad, Calif.) and Kodak Image station for reading and normalization of signal intensities. RNA specimens were isolated from resected tumors and matched healthy peritoneum specimens. PPIA, an invariantly expressed gene, was used to ensure equal loading. The following primers were used: PPP6CF: 5'-AGTATGTG-GAAATAGCGCGG-3' (pos 91-110) (SEQ ID NO: 24); PPP6CR: AAAAATGGGTCAGCAGGATG (pos 1016-997, ref seq. NM_002721.3) (SEQ ID NO: 25); PPIAF: 5'-TCT-GAGCACTGGAGAGAAAGG-3' (pos 197-217) (SEQ ID NO: 26); PPIAR: 5'-GGAAAACATGGAACCCAAAGG-3' (pos 717-697, ref. seq. NM_021130.3) (SEQ ID NO: 27).

1.10 Mapping of miR-31 in the 9p21.3 Deletion

Figure 2:
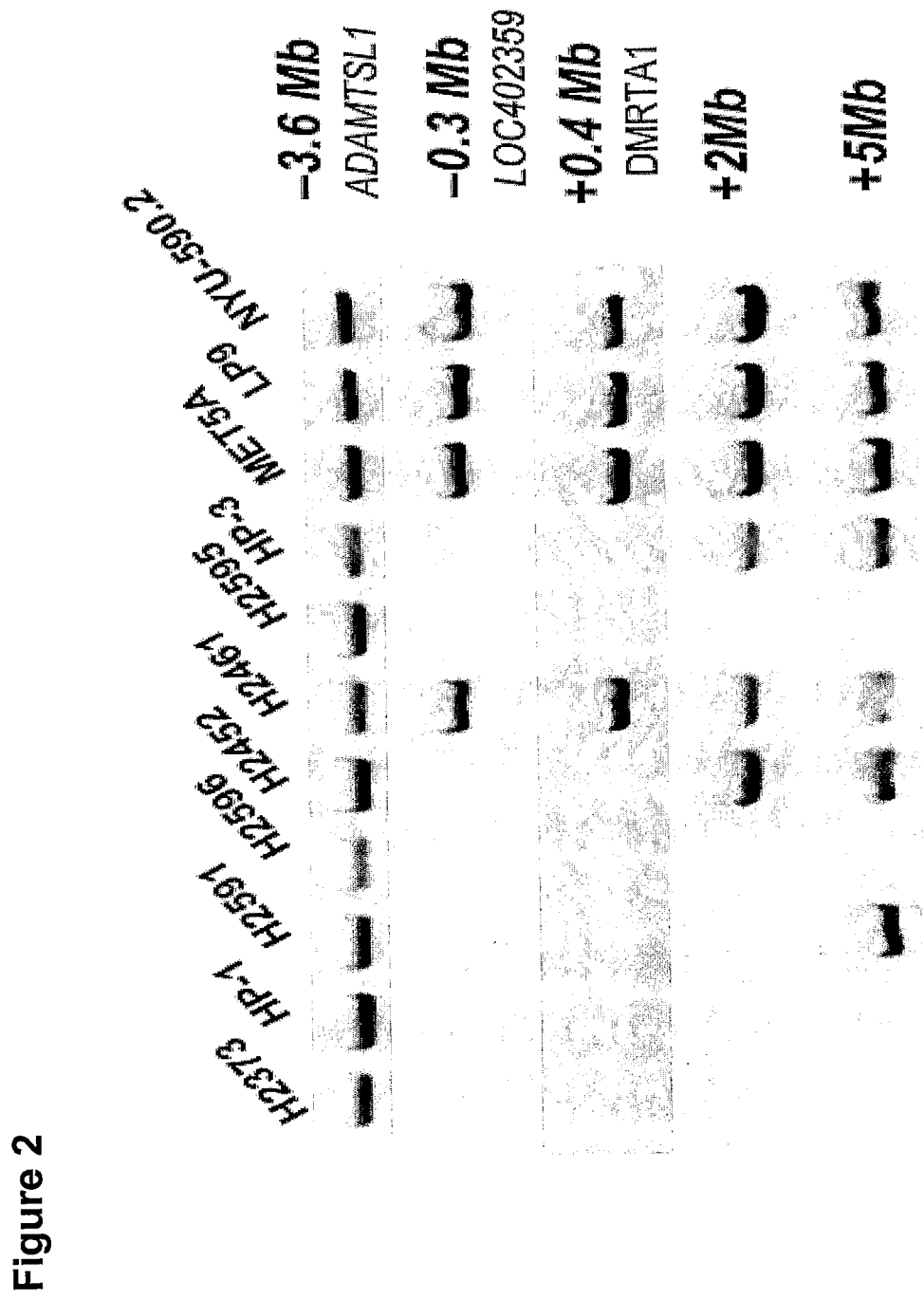
FIG. 2 shows mapping of the 9p21.3 deletion in malignant mesothelioma (MM) cell lines. Homozygous deletions were detected by PCR on the CDKN2A-neighboring genomic areas. Directions from CDKN2A toward telomere or centromere are indicated with (−) and (+), respectively. Lanes represent different cell lines. Malignant cell lines: H2373, HP-1, H2591, H2596, H2452, H2461, H2595, HP-3. Benign cell lines: MeT-5A, LP9 and NYU-590-2.

Mapping of miR-31 in the 9p21.3 deletion in clinical malignant mesothelioma specimens was achieved through whole-genome Representation Oligonucleotide Microarray Analysis (ROMA) data. Specimens included 22 mesothelioma specimens from patients with complete survival and progression information. Nine patients who had tumor recurrence/progression less than twelve months post-surgery was defined as the short-term recurrence group (STR), while thirteen patients who progressed after more than twelve months post-surgery was defined as the long-term recurrence group (LTR). The coordinates of the deletion in clinical specimens were assessed via processing of the ROMA data using CGH-Explorer software (Bioinformatics 2005; 21:821-822). The boundaries of homozygous 9p21.3 deletions in DNA specimens isolated from malignant mesothelioma cell lines were mapped via PCR on the genomic CDKN2A-flanking areas (FIG. 2) using primers listed in Table 1 below.

TABLE 1

Primers used for mapping homozygous deletions in 9p31.3

| Primer ID | Sequence | Positions on chr 9 (NT_008413.17) | SEQ ID NO |
|---|---|---|---|
| MIRN31F | CTTGAGGGTCCTATGGAGTCA | 21501265-21501285 | 6 |
| MIRN31R | GCCAGTCCTTCGTGTATTGC | 21502084-21502065 | 7 |
| CDKN2AF | GAATCCCGTAGCTTCCCTAC | 21958708-21958727 | 8 |
| CDKN2AR | CGGGTCCCGATTTAGAAGG | 21959726-21959708 | 9 |
| 9pminus1MbF | CCTGCTGTGCACTAGATCTC | 20999732-20999751 | 10 |
| 9pminus1MbR | AGGGCTCCCACTGATTCTG | 21000749-21000731 | 11 |
| 9pplus1MbF | GTTATGCTGCATTCCAGATGG | 22998493-22998513 | 12 |
| 9pplus1MbR | GTAATGCTTCCAGGTCTATGC | 22999510-22999490 | 13 |
| 9pminus2MbF | CACATCCTCTCCAGCATCTG | 20001250-20001269 | 14 |
| 9pminus2MbR | ACCTTCTGCCATGATTGTGAG | 20002270-20002250 | 15 |
| 9pplus2MbF | GAATGCTGCGGAGAAACATG | 24000266-24000285 | 16 |
| 9pplus2MbR | CACTGTGCAGATAAAGGGAAC | 24001285-24001265 | 17 |
| 9pplusSMbF | AAACGTAGCAGTCAGGAGGC | 26882677-26882658 | 18 |
| 9pplusSMbR | TCAACAGCGGGAATAACACA | 26881683-26881702 | 19 |
| 9p21LOC402359F | TGGGGATCCTTACAAAGTGC | 21685780-21685799 | 20 |
| 9p21LOC402359R | CTTCGTGTAGTCCTGCTGCC | 21686757-21686738 | 21 |

TABLE 1-continued

Primers used for mapping homozygous deletions in 9p31.3

| Primer ID | Sequence | Positions on chr 9 (NT_008413.17) | SEQ ID NO |
|---|---|---|---|
| 9p21 DMRTA1F | CCTTCCGAGTGGAAAGAGTG | 22436908-22436927 | 22 |
| 9p21 DMRTA1R | AACTATTCCTGCCCGCCTAT | 22437829-22437810 | 23 |

Example 1 miR-31 is not Expressed in Most Malignant Mesothelioma Cell Lines

Figure 3:
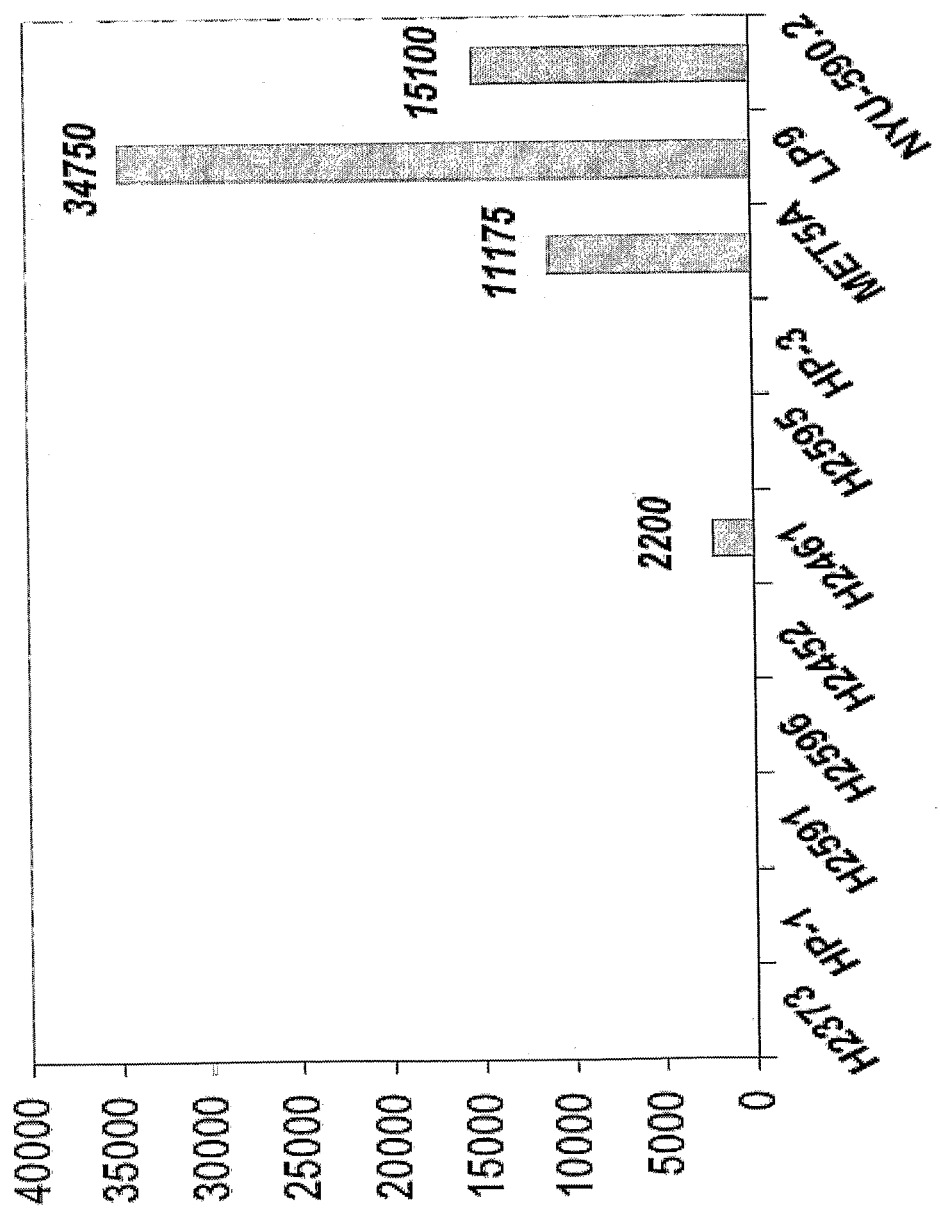
FIG. 3 shows expression of miR-31 (SEQ ID NO: 1) in malignant mesothelioma cell lines and control non-malignant mesothelial cells as determined by comparative miR microarray study. The y-axis depicts signal intensities in arbitrary units. Lanes represent different cell lines. Malignant cell lines: H2373, HP-1, H2591, H2596, H2452, H2461, H2595, HP-3. Benign cell lines: MeT-5A, LP9 and NYU-590-2.

To identify miRNAs whose expression is associated with malignant mesothelioma progression array analysis was performed on miRNAs expressed in eight cell lines established from malignant mesothelioma patients with poor prognosis, one SV40-transfected mesothelial cell line (MeT-5A), a Tert-immortalized cell line (LP9) and primary culture NYU-590.2 produced from a healthy peritoneum. Nine miRNAs were profoundly suppressed as compared to control mesothelial cells. One of these miRNAs, miR-31, showed no detectable expression in seven out of eight malignant mesothelioma cell lines, and a ~5-15-fold lower level in the remaining cell line H2461 (FIG. 3).

Example 2

Mapping of MIR31 inside the 9p21.3 Deletion in vivo and in vitro

Figure 4A:
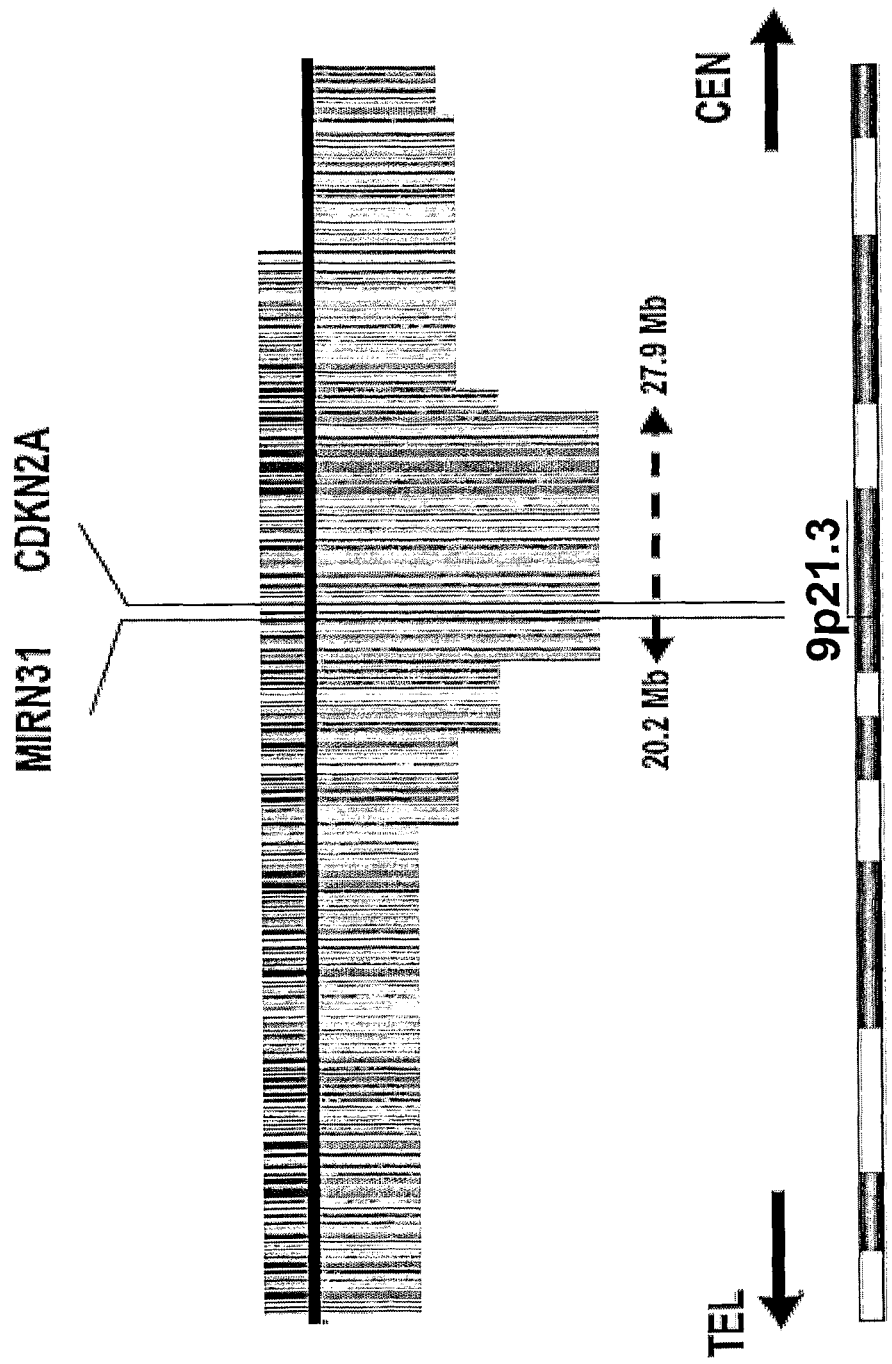
FIGS. 4A and B show co-deletion of miR-31 with cell cycle inhibitors CDKN2A (Gene ID 1029) and CDKN2B (Gene ID 1030) in 22 clinical specimens of malignant mesothelioma. 4A. Location of the miR-31 and CDKN2A genes in the vicinity of the telomeric boundary of the deletion. Losses are shown below the base line, gains above the baseline. The frequency of the deletion is ~32%. TEL: telomere; CEN: centromere. 4B. Seven out of thirteen patients with poor prognosis (STR group), but none of the LTR patients, show co-deletion of the CDKN2 genes with MIR31 in 9p21.3. STR: short-term recurrence (<12 months to relapse); LTR: long-term recurrence (≥12 months to relapse). Dashed lines represent deletions.

MIR31, the miR-31 encoding gene, is located in the 9p21.3 region proximally to CDKN2A and 2B, two tumor suppressor genes frequently deleted in malignant mesothelioma and other malignancies (Cheng et al., Cancer Res 1994; 54:5547-5551; Dacic et al., Virchows Arch 2008, 453:627-635; Murthy and Testa, J Cell Physiol 1999; 180:150-157; Lesueur et al., Br J Cancer 2008; 99:364-370; Usvasalo et al., Leuk Res 2008; 32:1228-1235; Grafstrom et al., Clin Cancer Res 2005; 11:2991-2997; Chang et al., J Urol 2003; 170:595-600). This deletion has previously been associated with poor prognosis for malignant mesothelioma patients (Ivanov et al., Int J Cancer 2009; 124:589-599). DNA copy number variation ROMA data produced on these specimens was analyzed and MIR31 was localized in the vicinity of the telomeric boundary of the common ~7.7 Mb deletion area (FIG. 4). MIR31 was found to be co-deleted with CDKN2A/2B in all seven patients from the short-term recurrence cohort that showed the deletion. Seven out of 13 STR, but none of LTR patients possessed the MIR31/CDKN2 co-deletion, suggesting that loss of miR-31 is a frequent event in malignant mesothelioma cells from patients with poor prognosis.

To answer whether homozygous MIR31 loss may be behind the observed silencing of miR-31 in malignant mesothelioma cell lines, PCR was performed on the MIR31- and CDKN2-flanking genomic regions using DNA isolated from the cell lines under study. These data were compared with miR-31 expression assessed by looped RT-PCR. As shown in FIG. 4, loss of miR-31 expression was linked with homozygous deletion of MIR31. All malignant mesothelioma cell lines under study were completely devoid of the CDKN2A gene and 7 out of 8 also showed MIR31 loss.

Figure 5A:
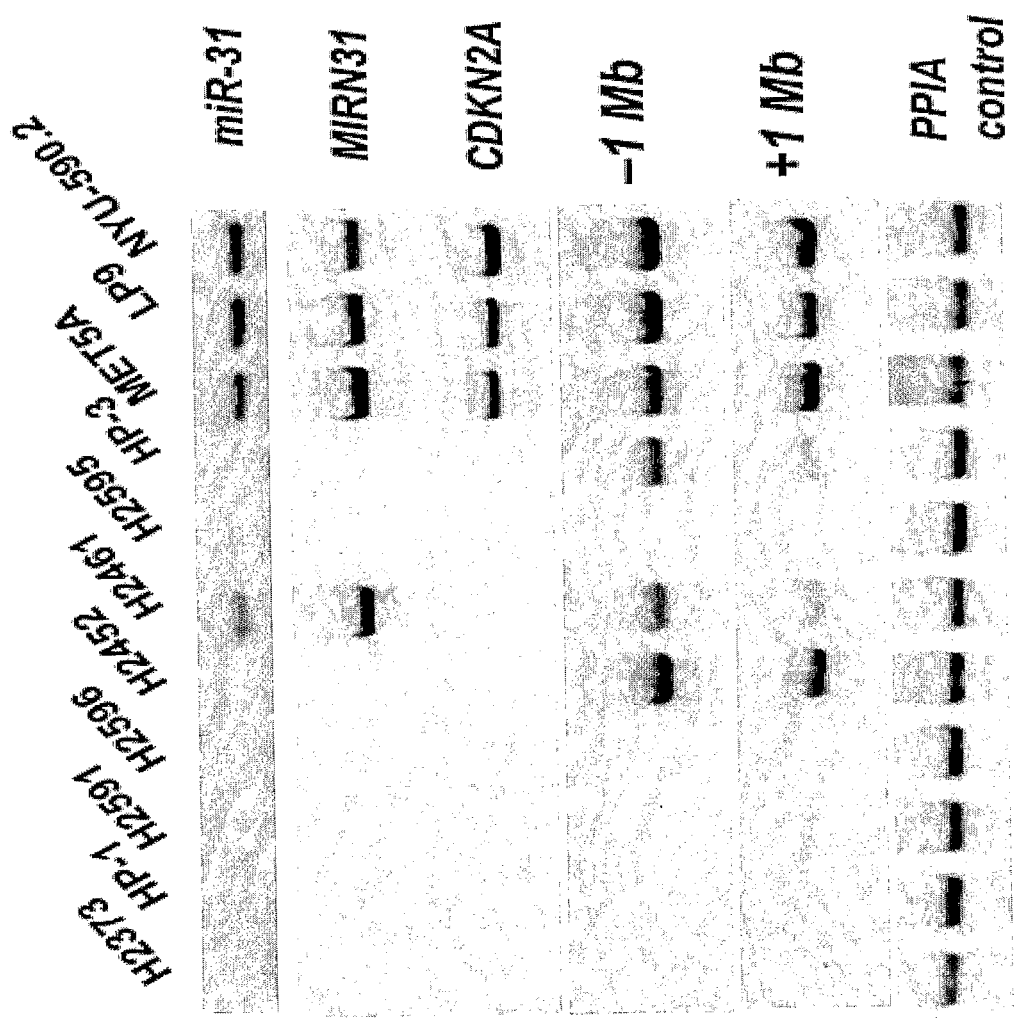
FIGS. 5A and B show mapping of homozygous co-deletion of MIR31 (Gene ID 407035) and CDKN2A in malignant mesothelioma cell lines. 5A. Comparison of looped RT-PCR assessment of miR-31 expression (upper panel) with genomic PCR (lower four panels) on the CDKN2A-neighboring area. Only one out of the eight malignant cell lines, H2461, shows miR-31 expression. None of the malignant cell lines expresses CDKN2A. Lanes represent different cell lines. Malignant cell lines: H2373, HP-1, H2591, H2596, H2452, H2461, H2595, HP-3. Benign cell lines: MeT-5A, LP9, NYU-590-2. 5B. Map of homozygous 9p21.3 deletions in malignant mesothelioma cell lines shows homozygous co-deletion of MIR31 with CDKN2A in seven out of eight malignant mesothelioma cell lines. Homozygous CDKN2A deletion in H2461 is the smallest and does not include MIR31.
Figure 5B:
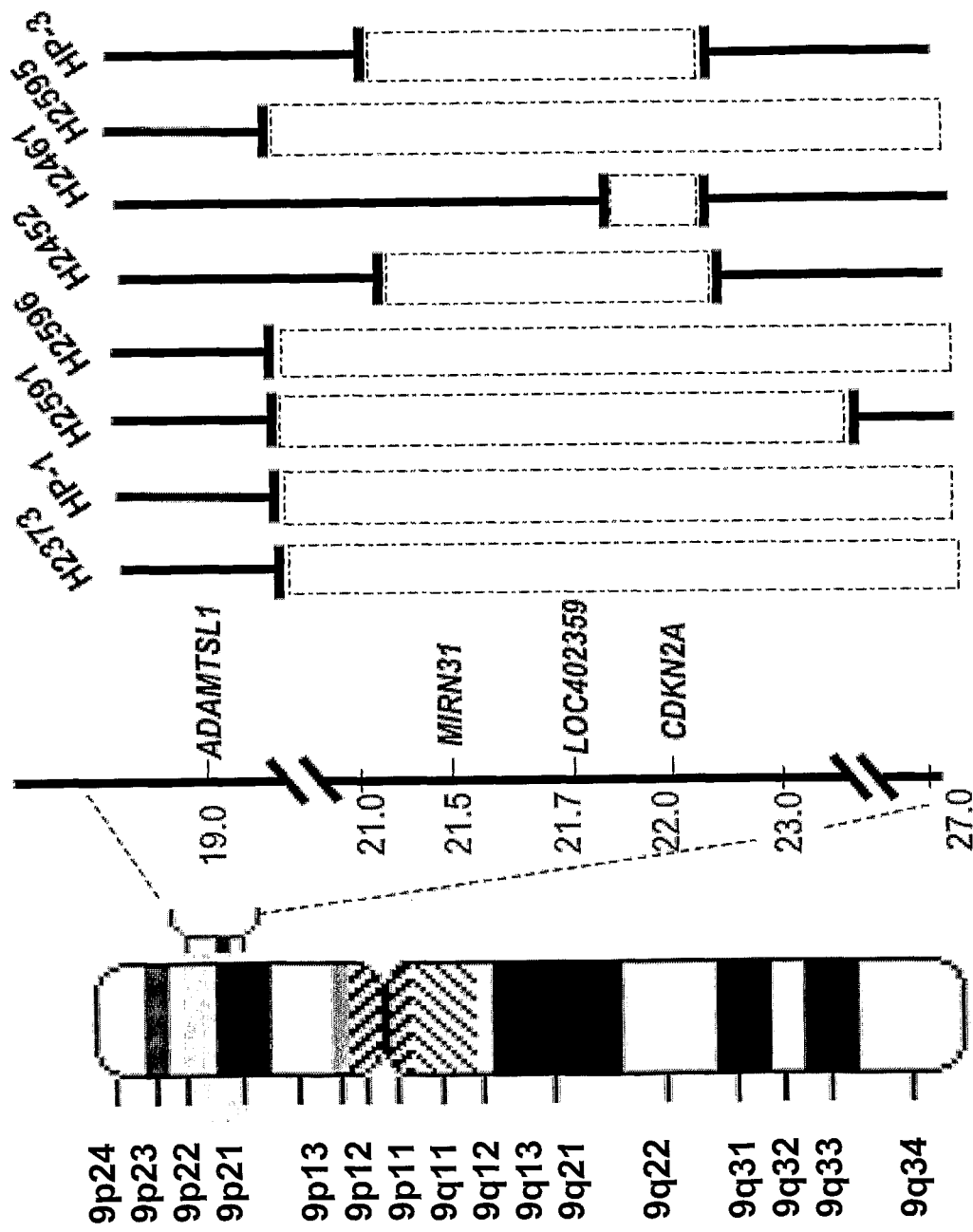
Figure 6A:
FIGS. 6A-D are bar charts showing suppressive effects of miR-31 on tumorigenic cell behaviors in H2595 (left) and HP-1 (right) mesothelioma cell lines, including reduction in invasive, migratory, proliferative and colony formation properties. The white bars represent cells treated with lipofectamine only. The crosshatched bars represent cells transfected with negative control oligonucleotide and the hatched bars represent cells transfected with miR-31 mimic (p<0.005).
Figure 6B:
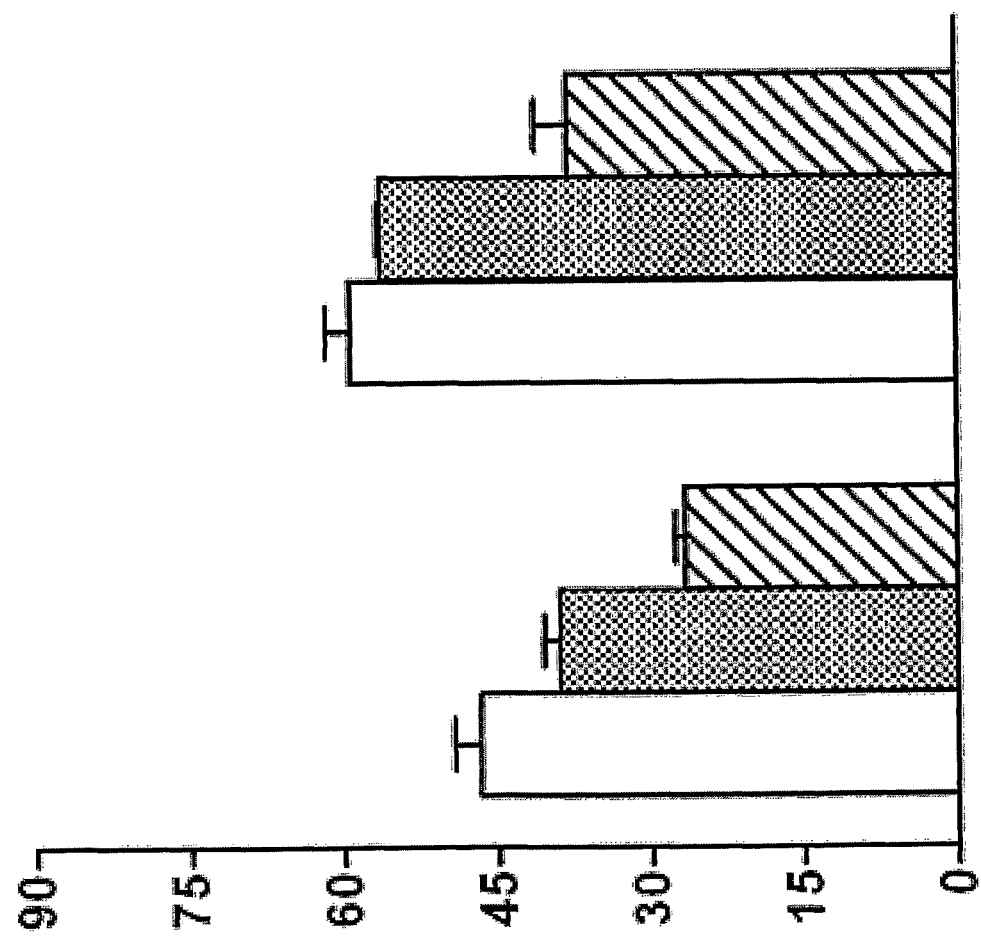
Figure 6C:
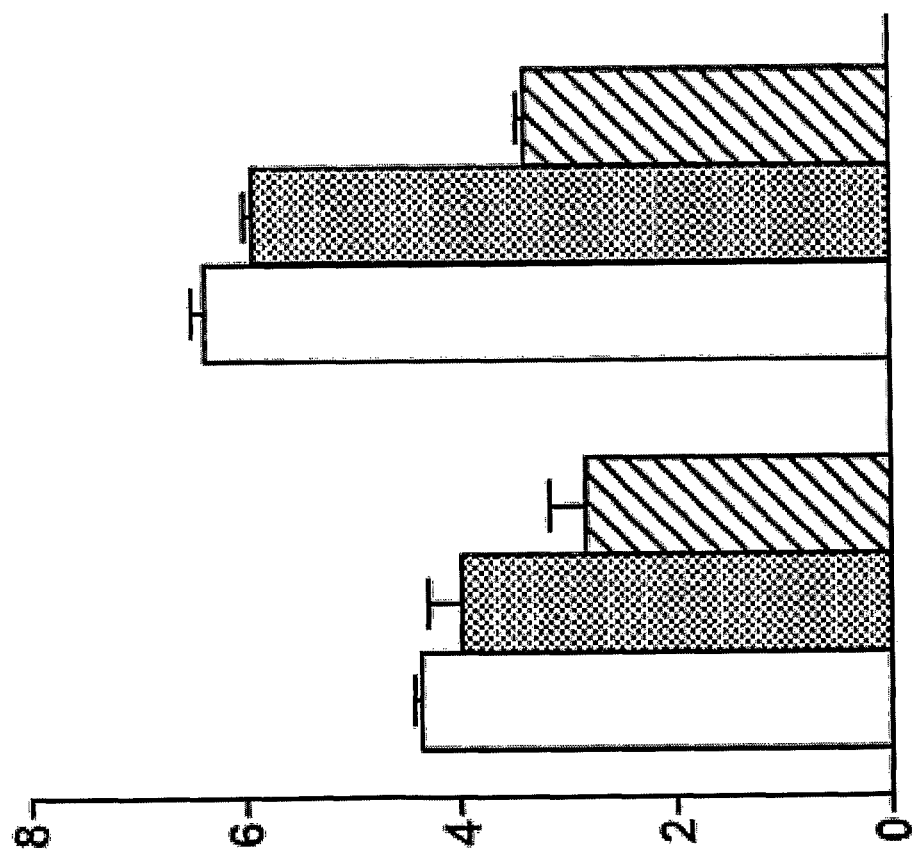
Figure 6D:
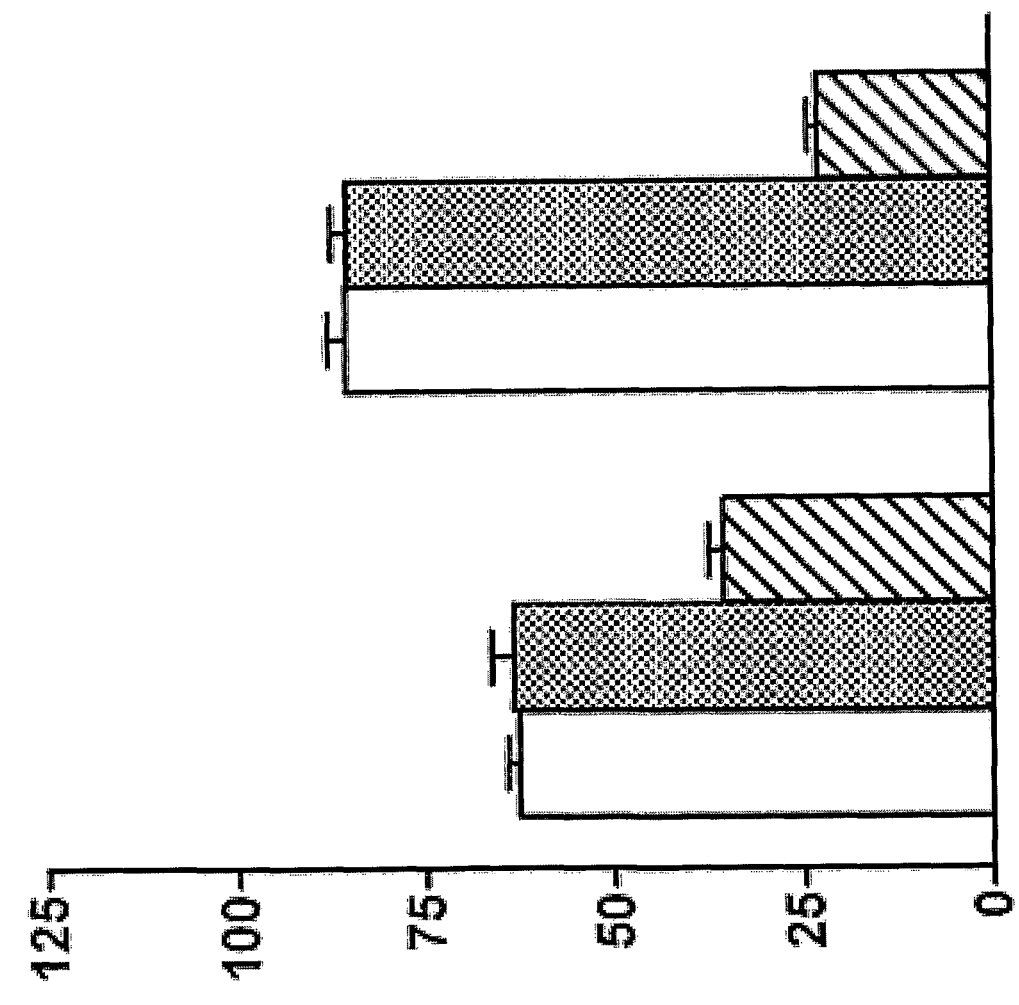

MiR-31-expressing H2461 was the only malignant mesothelioma cell line that possessed at least one copy of MIR31. Based on the PCR mapping shown in FIGS. 2 and 5A and B, the homozygous deletion area in malignant mesothelioma cell lines was estimated to span from less than 0.7 Mb in H2461 to ~2 Mb in H2452 and HP-3, 3-8 Mb in H2591, and to up to more than 6 MB in HP-1, H2373, H2596, and H2595. Lack of the 9p21.3 deletion in all controls including highly proliferating but benign (i.e., not capable of producing xenografted tumors) MeT-5A cells argued that the observed pattern was not due to cell culture artifacts.

Example 3

Re-introduction of miR-31 into Malignant Mesothelioma Cells Suppresses their Tumorigenic Properties Based on the fact that miR-31 belongs to the area of recurrent deletion in malignant mesothelioma and is not expressed in the majority of the malignant mesothelioma cell lines used herein, the question was whether this miR possesses tumor suppressor properties. To test this possibility, miR-31 was re-introduced into H2595 and HP-1 cell lines, which are devoid of this miR, and its effect on cell behavior was analyzed. In vitro functional studies showed that invasive, migratory, proliferative and colony formation properties of both cell lines were markedly reduced upon miR-31 introduction as compared to the lipofectamine only or negative control oligonucleotide, suggesting that miR-31 may be tumor-suppressive (FIG. 6).

Example 4 miR Inhibits Progression of Malignant Mesothelioma Cells to S-Phase

Figure 7A:
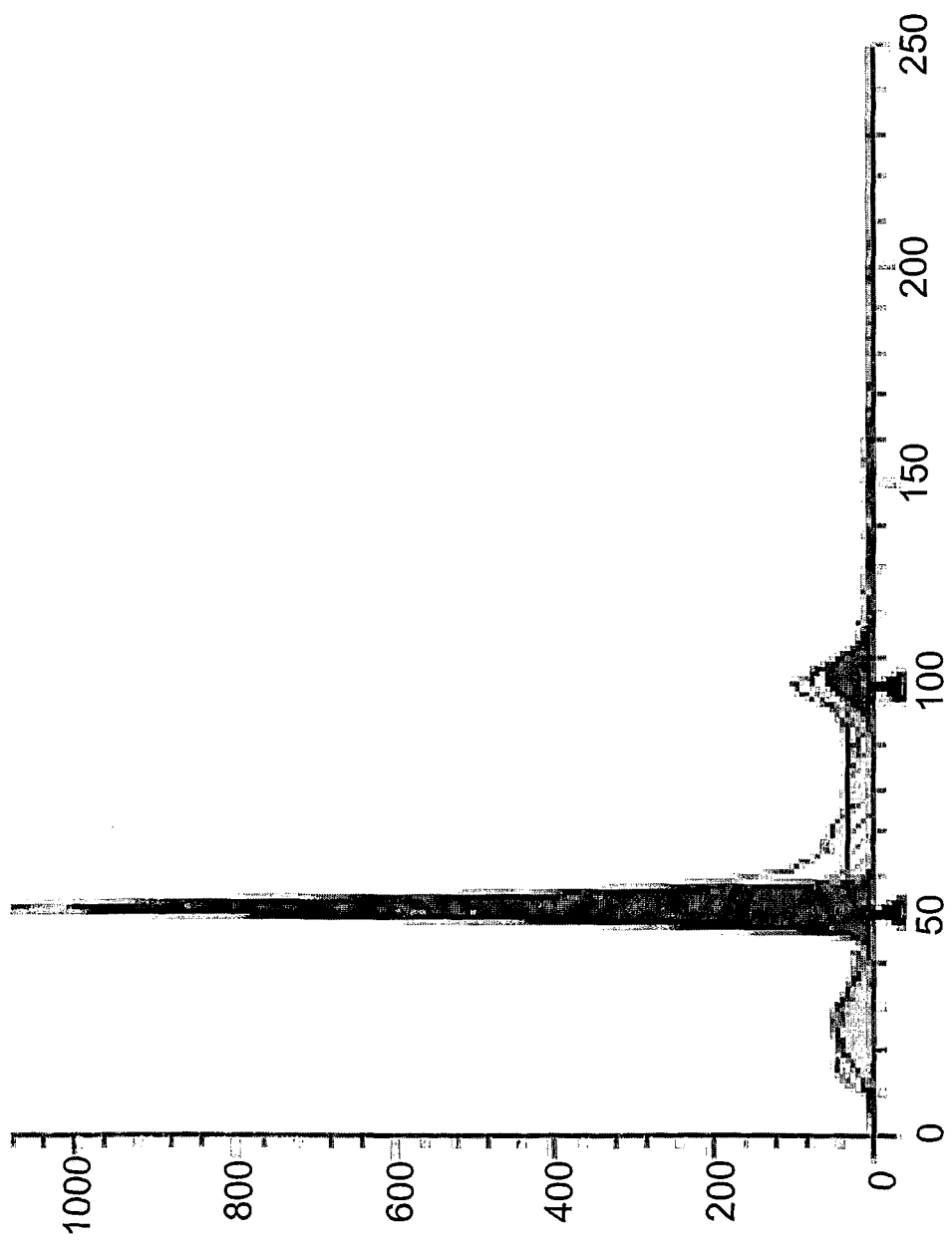
Figure 7B:
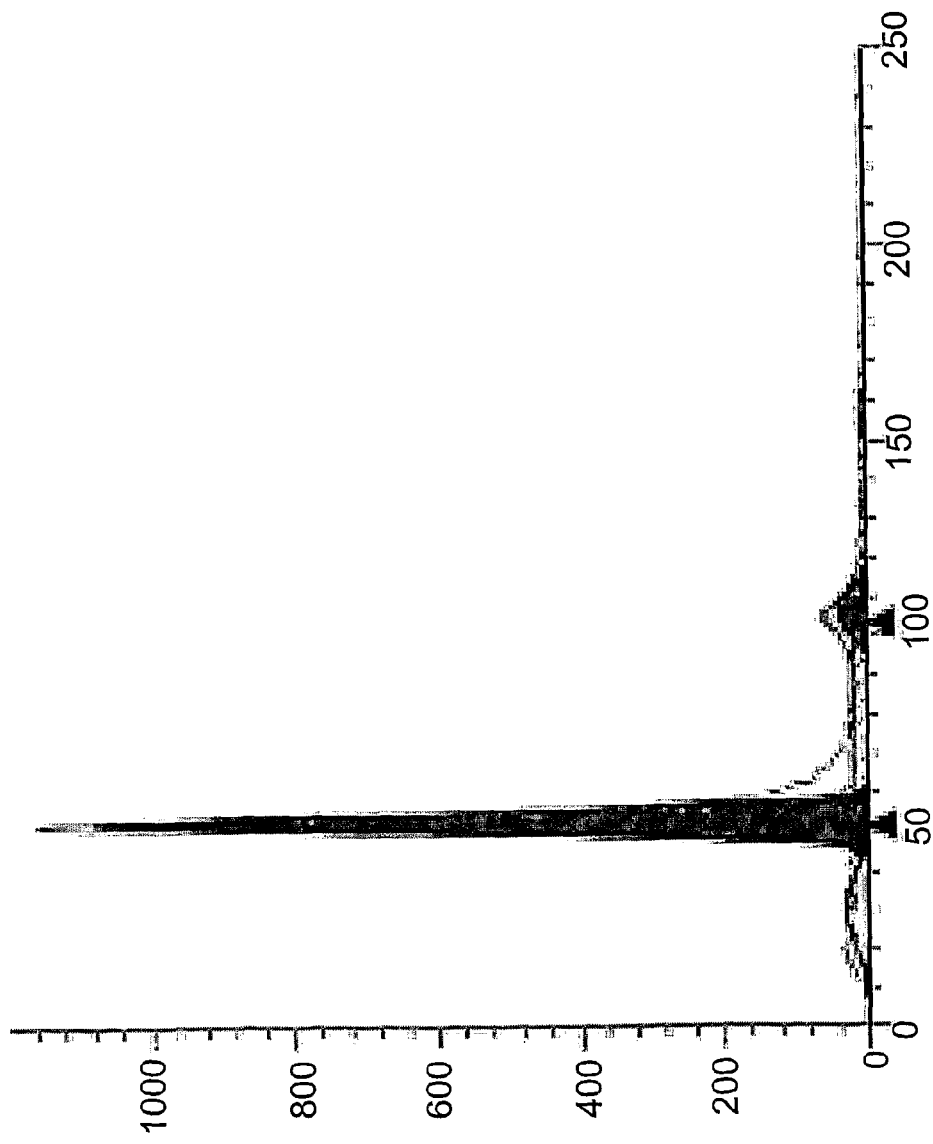
Figure 7C:
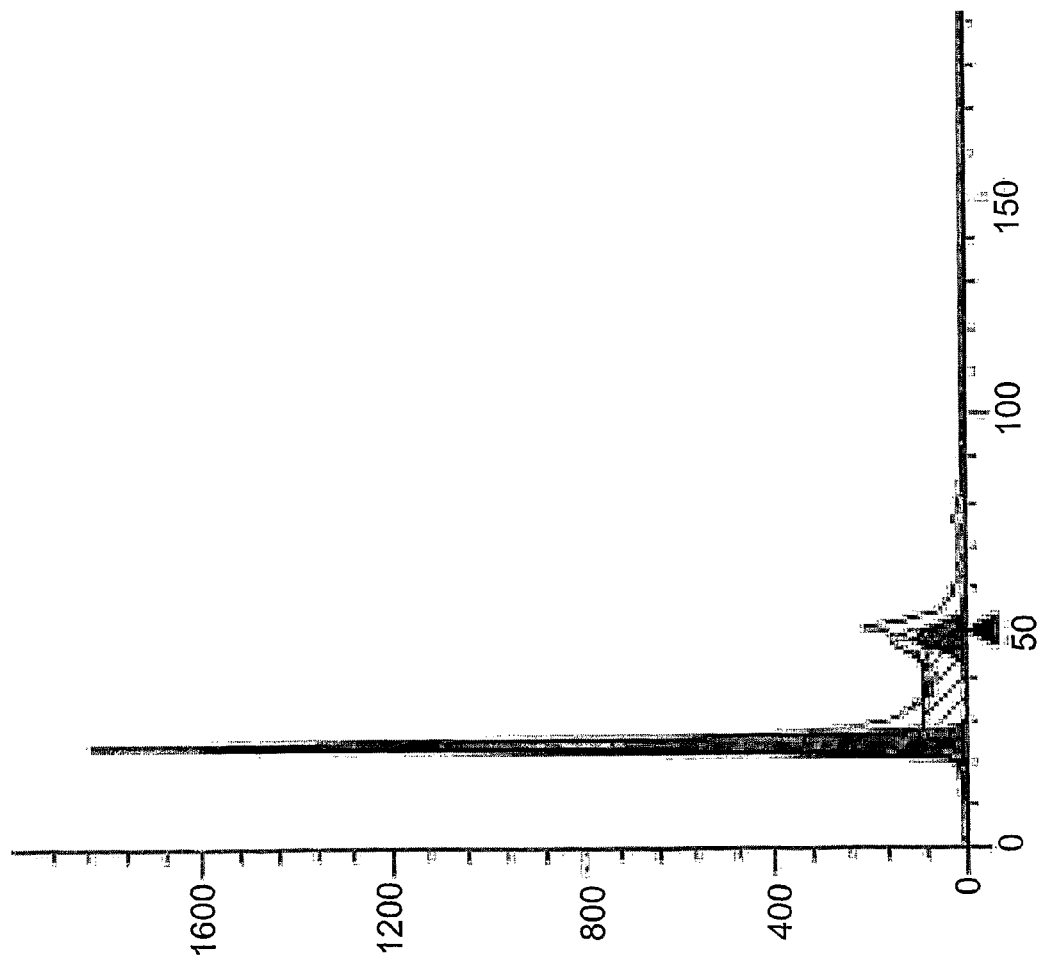

To provide more detailed insight into the anti-proliferative propensity of miR-31 its impact on cell cycle progression was analyzed using flow-cytometry analysis of cells stained with propidium iodide. In this experiment, HP-1 cells, which are devoid of miR-31, were used for miR-31 re-introduction, and H2461 cells, which retain a modest level of endogenous miR-31 expression, were used for transfection with the miR-31 inhibitor. In both cases the cellular amount of miR-31 was monitored via looped RT-PCR. As shown in FIGS. 7A and 7B, re-introduction of miR-31 into HP-1 cells produced a ~27% reduction of cells in S-phase (from 18.8% to 13.8%), while transfection of the miR-31 inhibitor into H2461 cells produced the opposite effect on the S-phase cells with a similar amplitude (from 25.1% to 34.4%) (FIGS. 7C and 7D). MiR-31 also caused a 7.2% increase in the G1 ratio in HP-1 cells, while its inhibitor produced a 20.2% decrease in G1 in H2461. Finally, H2461 cells showed a significant increase in the G2/M cells caused by the miR inhibitor. In summary, this cell cycle analysis demonstrated that both exogenous and endogenous miR-31 profoundly and reproducibly affected cell cycle progression in malignant mesothelioma cells devoid of the CDKN2A and CDKN2B genes.

Example 5

Enrichment of Potential miR-31 Targets with Cell Cycle Regulators

Figure 8B:
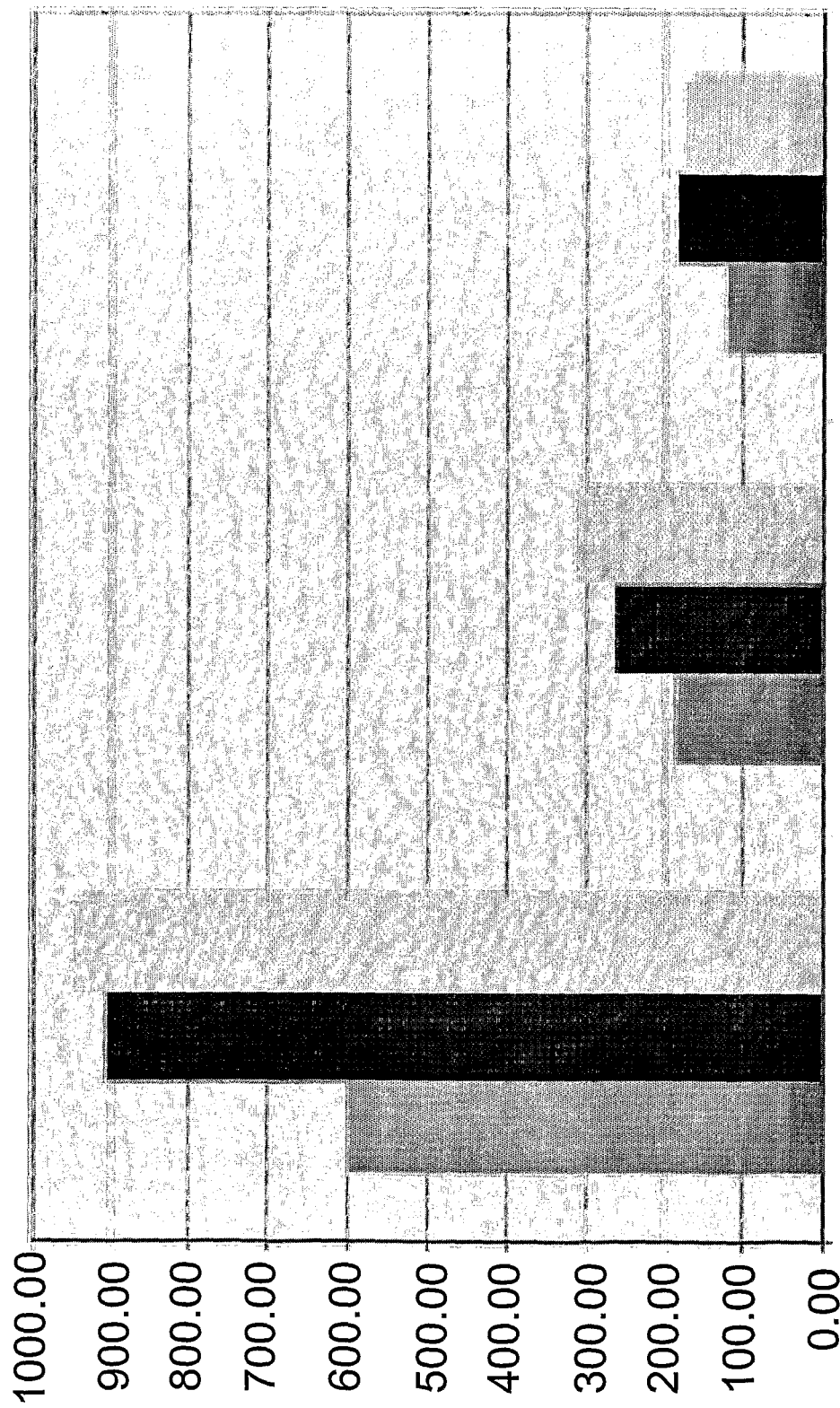

Computational prediction of miR binding sites generated hundreds of potential genes that need validation. To characterize possible targets of miR-31, HP-1 cells transfected with miR-31 were used to study global expression array. Proper delivery of the miR into the cells was ensured by looped RT-PCR. Microarray-assisted analysis identified 1145 Affymetrix probes that showed a ~1.33 to 10-fold down-regulation upon miR-31 delivery into these cells as compared to negative control oligonucleotide and lipofectamine only. To increase statistical power and identify cellular processes involved in miR-31 activity, hypergeometric analysis of these data was performed. Using GenoCodis 2.0 portal, these probes were associated with 650 GO annotated genes and three types of analyses were performed: 1) search for predicted miR targets; 2) GO Biological Profiling; and 3) GO KEGG profiling. The search for miR targets revealed that the 650 gene set is highly enriched with computationally predicted miR-31 targets (60 miR-31 targets with a corrected hypergeometric Hyp* value of ~$1.9 \times 10^{-22}$ (Table 2). This observation suggested that this method produced biologically relevant information and encouraged further investigation into possible roles of these 650 candidate miR-31 targets in tumor growth. GO Biological Profiling analysis identified among 650 genes DNA Replication (21 genes), Cell Cycle (33 genes), DNA Repair (21 genes), and Response to DNA Damage Stimulus (24 genes) as the four most statistically significant groups (Tables 3 and 4). These results further affirmed the link suggested between miR-31 and regulation of cell proliferation by the functional studies presented here. To identify cellular processes that may involve putative miR-31 targets KEGG GO profiling of the same 650 candidate genes was performed. "Cell Cycle" (18 genes, Hyp*=$1.7 \times 10^{-11}$), "DNA Replication" (11 genes, Hyp*=$7.2 \times 10^{-10}$), and "p53 Signaling Pathway" groups (13 genes, Hyp*=$3.7 \times 10^{-9}$) were the most statistically relevant processes. As shown in FIGS. 8B and C, genes from the first two groups encode essential components that coordinate cell division with DNA replication. In the next step, RNA22 MicroRNA Target Detection interface (Cell 2006; 126:1203-1217) was used to screen 18 genes from the KEGG "Cell Cycle" group for miR-31 binding sites. As shown in Table 5, half of these genes possess miR-31-binding sites in their mRNAs, which show favorable thermodynamics. These data imply that miR-31 may directly or indirectly control a coordinately functioning set of genes that orchestrate DNA replication, DNA repair, and cell proliferation.

TABLE 2

Statistically significant prevalence of predicted miR-31 targets in the set of genes suppressed by miR-31 in HP-1 cells

| Genes | NGR | NG | Hyp | Hyp* | Annotations |
|---|---|---|---|---|---|
| 60 genes | 669(37435) | 60(650) | 2.71E−25 | 1.92E−22 | (microRNA) hsa-miR-31 |
| 42 genes | 637(37435) | 42(650) | 2.27E−13 | 8.07E−11 | (microRNA) hsa-miR-583 |
| 47 genes | 873(37435) | 47(650) | 1.12E−11 | 2.66E−09 | (microRNA) hsa-miR-200a |
| 42 genes | 743(37435) | 42(650) | 3.21E−11 | 5.71E−09 | (microRNA) hsa-miR-873 |
| 42 genes | 832(37435) | 42(650) | 1.00E−09 | 1.43E−07 | (microRNA) hsa-miR-519e |
| 38 genes | 705(37435) | 38(650) | 1.07E−09 | 1.27E−07 | (microRNA) hsa-miR-182 |
| 42 genes | 863(37435) | 42(650) | 2.93E−09 | 2.98E−07 | (microRNA) hsa-miR-200b |

NGR—number of annotated genes in the reference list (total number of genes in the reference list);

NG—number of annotated genes in the input list of 650 genes suppressed by miR-31;

Hyp—hypergeometric p value;

Hyp*—corrected hypergeometric p value.

TABLE 3

Statistically significant biological groups detected within genes suppressed by miR-31

| Genes | NGR | NG | Hyp | Hyp* | Annotations |
|---|---|---|---|---|---|
| 21 genes | 126(37435) | 21(650) | 6.14E−15 | 0.00000000000168345 | DNA replication |
| 33 genes | 376(37435) | 33(650) | 3.64E−14 | 0.00000000000498527 | Cell cycle |
| 21 genes | 146(37435) | 21(650) | 1.27E−13 | 0.0000000000115568 | DNA repair |
| 24 genes | 214(37435) | 24(650) | 6.13E−13 | 0.0000000000419705 | Response to DNA damage |

TABLE 4

List of genes that belong to four major biological groups detected within miR-31-suppressed genes.

DNA REPLICATION

| # | Gene | Description |
|---|---|---|
| 1 | RFC4 | Replication factor C subunit 4 |
| 2 | MCM7 | DNA replication licensing factor MCM7 |
| 3 | MCM5 | DNA replication licensing factor MCM5 |
| 4 | PRIM1 | DNA primase small subunit |
| 5 | DTL | Denticleless protein homolog |
| 6 | CHEK1 | Serine/threonine-protein kinase Chk1 |
| 7 | RBMS1 | RNA-binding motif, single-stranded-interacting protein 1 |
| 8 | POLQ | DNA polymerase theta (DNA polymerase eta) |
| 9 | RAD1 | Cell cycle checkpoint protein RAD1 |
| 10 | TYMS | Thymidylate synthase |
| 11 | BLM | Bloom syndrome protein |
| 12 | CHAF1A | Chromatin assembly factor 1 subunit A |
| 13 | RAD9A | Cell cycle checkpoint control protein RAD9A |
| 14 | FEN1 | Flap endonuclease 1 |
| 15 | MCM6 | DNA replication licensing factor MCM6 (p105MCM) |
| 16 | TK1 | Thymidine kinase, cytosolic |
| 17 | MCM3 | DNA replication licensing factor MCM3 |
| 18 | MCM10 | Protein MCM10 homolog (HsMCM10) |
| 19 | ORC4L | Origin recognition complex subunit 4 |
| 20 | MCM2 | DNA replication licensing factor MCM2 |
| 21 | CTGF | Connective tissue growth factor precursor |

CELL CYCLE

| # | Gene | Description |
|---|---|---|
| 1 | CCNA1 | Cyclin-A1 |
| 2 | MCM7 | DNA replication licensing factor MCM7 |
| 3 | SGOL1 | Shugoshin-like 1 (hSgo1) |
| 4 | LLGL2 | Lethal(2) giant larvae protein homolog 2 |
| 5 | CLASP2 | CLIP-associating protein 2 |
| 6 | CCNDBP1 | Cyclin-D1-binding protein 1 |
| 7 | TFDP2 | Transcription factor Dp-2 |
| 8 | NEK6 | Serine/threonine-protein kinase Nek6 |
| 9 | CHEK1 | Serine/threonine-protein kinase Chk1 |
| 10 | E2F8 | Transcription factor E2F8 (E2F-8) |
| 11 | UBE2I | SUMO-conjugating enzyme UBC9 |
| 12 | FOXM1 | Forkhead box protein M1 |
| 13 | HELLS | Lymphoid-specific helicase |
| 14 | CHAF1A | Chromatin assembly factor 1 subunit A |
| 15 | TACC1 | Transforming acidic coiled-coil-containing protein 1 |
| 16 | DUSP1 | Dual specificity protein phosphatase 1 |
| 17 | H2AFX | Histone H2A.x (H2a/x) |
| 18 | SMPD3 | Sphingomyelin phosphodiesterase 3 |
| 19 | PPP6C | Serine/threonine-protein phosphatase 6 catalytic subunit (PP6C) |
| 20 | MAP3K8 | Mitogen-activated protein kinase kinase kinase 8 |
| 21 | CDK2 | Cell division protein kinase 2 |
| 22 | MCM6 | DNA replication licensing factor MCM6 (p105MCM) |
| 23 | ARHGEF2 | Rho guanine nucleotide exchange factor 2 |
| 24 | RCC1 | Regulator of chromosome condensation |
| 25 | MCM3 | DNA replication licensing factor MCM3 |
| 26 | JUB | Protein ajuba |
| 27 | NEDD9 | Enhancer of filamentation 1 (hEF1) |
| 28 | CCNE2 | G1/S-specific cyclin-E2 |
| 29 | CCNB2 | G2/mitotic-specific cyclin-B2 |
| 30 | CDC6 | Cell division control protein 6 homolog |
| 31 | MCM2 | DNA replication licensing factor MCM2 |
| 32 | CDC2 | Cell division control protein 2 homolog |
| 33 | PRR6 | Proline-rich protein 6 (Nuclear protein p30) |

DNA REPAIR

| # | Gene | Description |
|---|---|---|
| 1 | RFC4 | Replication factor C subunit 4 |
| 2 | GADD45A | Growth arrest and DNA-damage-inducible protein GADD45 alpha |
| 3 | C1orf124 | Zinc finger RAD18 domain-containing protein C1orf124 |
| 4 | HMGB1 | High mobility group protein B1 |
| 5 | APLF | Aprataxin and PNK-like factor |
| 6 | SETMAR | Histone-lysine N-methyltransferase SETMAR |
| 7 | CHEK1 | Serine/threonine-protein kinase Chk1 |
| 8 | POLQ | DNA polymerase theta (DNA polymerase eta) |
| 9 | RAD1 | Cell cycle checkpoint protein RAD1 |
| 10 | PARP1 | Poly [ADP-ribose] polymerase 1 (PARP-1) |
| 11 | TYMS | Thymidylate synthase |
| 12 | BLM | Bloom syndrome protein |
| 13 | RAD51 | DNA repair protein RAD51 homolog 1 |
| 14 | RAD18 | E3 ubiquitin-protein ligase RAD18 |
| 15 | CHAF1A | Chromatin assembly factor 1 subunit A |
| 16 | XRCC3 | DNA repair protein XRCC3 |
| 17 | RAD9A | Cell cycle checkpoint control protein RAD9A |
| 18 | H2AFX | Histone H2A.x (H2a/x) |
| 19 | POLE2 | DNA polymerase epsilon subunit 2 |
| 20 | RAD51L1 | DNA repair protein RAD51 homolog 2 |
| 21 | RBBP8 | Retinoblastoma-binding protein 8 (RBBP-8) |

RESPONSE TO DNA DAMAGE STIMULUS

| # | Gene | Description |
|---|---|---|
| 1 | MCM7 | DNA replication licensing factor MCM7 |
| 2 | GADD45A | Growth arrest and DNA-damage-inducible protein GADD45 alpha |
| 3 | MLH1 | DNA mismatch repair protein Mlh1 (MutL protein homolog 1) |
| 4 | BRE | Protein BRE (Brain and reproductive organ-expressed protein)(BRCA1/BRCA2-containing complex subunit 45) |
| 5 | DTL | Denticleless protein homolog |
| 6 | APLF | Aprataxin and PNK-like factor |
| 7 | SETMAR | Histone-lysine N-methyltransferase SETMAR |
| 8 | CHEK1 | Serine/threonine-protein kinase Chk1 |
| 9 | NEIL1 | Endonuclease VIII-like 1 (Nei-like 1) |
| 10 | POLQ | DNA polymerase theta |
| 11 | RAD1 | Cell cycle checkpoint protein RAD1 |
| 12 | PARP1 | Poly [ADP-ribose] polymerase 1 |
| 13 | BLM | Bloom syndrome protein |
| 14 | UBE2N | Ubiquitin-conjugating enzyme E2 N |
| 15 | RAD51 | DNA repair protein RAD51 homolog 1 |
| 16 | RAD18 | E3 ubiquitin-protein ligase RAD18 |
| 17 | CHAF1A | Chromatin assembly factor 1 subunit A |
| 18 | XRCC3 | DNA repair protein XRCC3 |
| 19 | RAD9A | Cell cycle checkpoint control protein RAD9A |
| 20 | H2AFX | Histone H2A.x (H2a/x) |
| 21 | EXO1 | Exonuclease 1 |
| 22 | RAD51L3 | DNA repair protein RAD51 homolog 4 |
| 23 | BARD1 | BRCA1-associated RING domain protein 1 |
| 24 | RAD51L1 | DNA repair protein RAD51 homolog 2 |

Example 6

Clinical Validation of Potential miR-31 Targets Linked with Cell Cycle Regulation To evaluate clinical significance of KEGG Cell Cycle genes affected by miR-31, their expression was assessed in a collection of 32 specimens of malignant mesothelioma and 7 healthy peritoneum controls. This comparison showed that half of these genes are up-regulated in malignant mesothelioma (see column 5 in Table 5) compared to normal mesothelium. The Oncomine portal was also used to evaluate whether these genes may serve as markers for other cancers. Table 5 shows that 13 out of 18 KEGG Cell Cycle are reliable discriminators between different breast cancer grades. This conclusion is based on multiple independent studies that all show extremely low p values for the null hypothesis. Similarly, assessment of KEGG DNA Replication genes enabled classification of RFC3, POLE2, PRIM1, RFC4, and FEN1 as reliable breast cancer prognostic markers. According to Oncomine, other malignancies, such as mesothelioma, ovarian, and bladder cancers repeatedly showed over-expression of miR-31-affected KEGG genes as compared to normal tissues. Thus, genes identified as putative miR-31 targets may play common roles in poor-prognostic malignant mesothelioma, breast, and other cancers.

TABLE 5

Analysis of KEGG Cell Cycle genes for miR-31 binding sites, over-expression in malignant mesothelioma and validation as prognostic markers for breast cancer

| GENE ID | Description | miR-31 binding site/ Folding energy | miR-31 alignment with target | Validation in MM (fold up-regulation)* | Validation in breast carcinoma** |
|---|---|---|---|---|---|
| CCNA1 | Cyclin-A1 | NM_003914.3, pos. 1511-1531; -33.3 Kcal/mol | AGCTGCAGCAGCTTTTTGCCT<br>\|\|\|\|\|     \|\|\|\|   \|\|\|\|\|\|\|\|\|<br>UCGAUACGGUCGUAGAACGGA | | |
| CCNB2 | G2/mitotic-specific cyclin-B2 | NM_004701.2, pos. 1076-1096; -27.1 Kcal/mol | GCAGCT--GCTTCCTGCTTGTCT<br>\|\|\|\|  \|\|\|    \|\|\|\|\|\|\|\|<br>--UCGAUACGGUCGUAGAACGGA | 12.4, p = 0.02 | Prognostic, 8 studies; p~1E-50 |
| CCNE2 | G1/S-specific cyclin-E2 | Not found | | | Prognostic, 6 studies; p~1E-9 |
| CDC2 | Cell division control protein 2 homolog | NM_001786.3, pos. 1607-1627; -25.5 Kcal/mol | AGAGC-ATGCCAA-AATTTGCTA<br>\|\|\|  \|\|\|\|\|\|\|  \|  \|\|\|\|\|\|\|\|<br>--UCGAUACGGUCGUAGAACGGA | 1.9; p = 0.03 | Prognostic, 9 studies; p~1E-50 |
| CDC6 | Cell division control protein 6 homolog | Not found | | 3.2; p = 0.04 | Prognostic, 7 studies; p~1E-13 |
| CDK2 | Cell division protein kinase 2 | NM_001798.3, pos. 1649-1669; -33.5 Kcal/mol | ACCCTA-GTTAGTGTTTTGCCT<br>\|\|\|  \|\|\|\|\|\|\|\|\|\|\|\|\|\|\|\|<br>UC-GAUACGGUCGUAGAACGGA | | Prognostic, 6 studies; p~4E-6 |
| CHEK1 | Serine/threonine-protein kinase Chk1 | Not found | | 7.1; p = 0.001 | Prognostic, 8 studies; p~1E-50 |
| GADD45A | Growth arrest and DNA-damage-inducible protein GADD45 alpha | Not found | | | |
| GADD45B | Growth arrest and DNA-damage-inducible protein GADD45 beta | Not found | | | |
| MCM2 | DNA replication licensing factor MCM2 | NM_004526.2, pos. 2994-3014; -27 Kcal/mol | TGGT--TGCTGAACATCTTGCCA<br>\|\|\|   \|\|\|\|       \|\|\|\|\|\|\|\|\|<br>-UCGAUACGGUC-GUAGAACGGA | 4.8; p = 0.002 | Prognostic, 8 studies; p~1E-50 |
| MCM3 | DNA replication licensing factor MCM3 | Not found | | 1.57; p = 0.004 | Prognostic, 6 studies; p~6E-12 |
| MCM5 | DNA replication licensing factor MCM5 | NM_006739.3, pos. 1610-1630; -28 Kcal/mol | TTC-ATGCCCACCATCTTGTCG<br>\|\|\|\|\|       \|\|\|\|\|\|\|\|\|\|<br>UCGAUACGGUC-GUAGAACGGA | 1.67; p = 0.03 | Prognostic, 7 studies; p~1E-11 |
| MCM6 | DNA replication licensing factor MCM6 | Not found | | 1.87; p = 0.01 | Prognostic, 9 studies; p~1E-50 |
| MCM7 | DNA replication licensing factor MCM7 | NM_005916.3, pos. 725-745; -26.8 Kcal/mol | GCTACGCGAAGCTCTTTGCTG<br>\|\|\|\|\|  \|\|   \|\|    \|\|\|\|\|\|<br>UCGAUACGG-UCGUAGAACGGA | | Prognostic, 6 studies; p~2E-9 |
| ORC4L | Origin recognition complex subunit 4 | NM_181742.1, pos. 1580-1600; -33.9 Kcal/mol | TGTCTTGGCTGTGTCTTGCCT<br>\|\|  \|\|   \|\|\|\|\|\|\|\|\|\|\|\|<br>UCGAUACGGUCGUAGAACGGA | | |

TABLE 5-continued

Analysis of KEGG Cell Cycle genes for miR-31 binding sites, over-expression in malignant mesothelioma and validation as prognostic markers for breast cancer

| GENE ID | Description | miR-31 binding site/ Folding energy | miR-31 alignment with target | Validation in MM (fold up-regulation)* | Validation in breast carcinoma** |
|---|---|---|---|---|---|
| SFN | 14-3-3 protein sigma (Stratifin) | Not found | | | |
| SKP2 | S-phase kinase-associated protein 2 (F-box protein Skp2) | Not found | | 4.1; p = 0.001 | Prognostic, 5 studies; p~1E-14 |
| YWHAH | 14-3-3 protein eta (Protein AS1) | NM_003405.3, pos. 1506-1526; -27.7 Kcal/mol | AGTAGCT---CCTTGGTTTTGCCT<br>\|\|\|\|    \|\|    \|\|\|\|\|\|\|\|\|<br>---UCGAUACGGUCGUAGAACGGA | | |

Last two columns represent data produced on 32 malignant mesothelioma specimens and the results of profiling of multiple sets of Oncomine breast cancer data. Approximate p values from selected studies are shown in last column.

Example 7

Figure 8C:
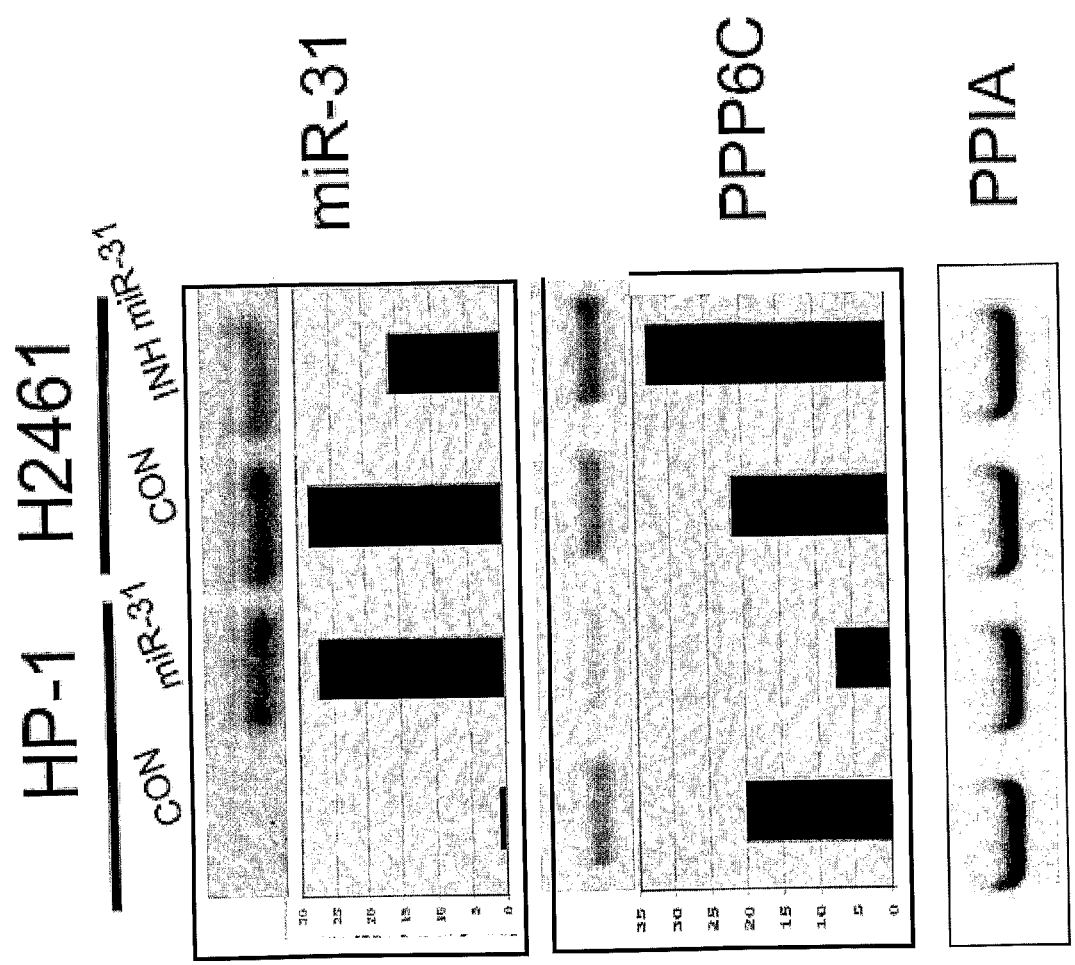
Figure 8D:
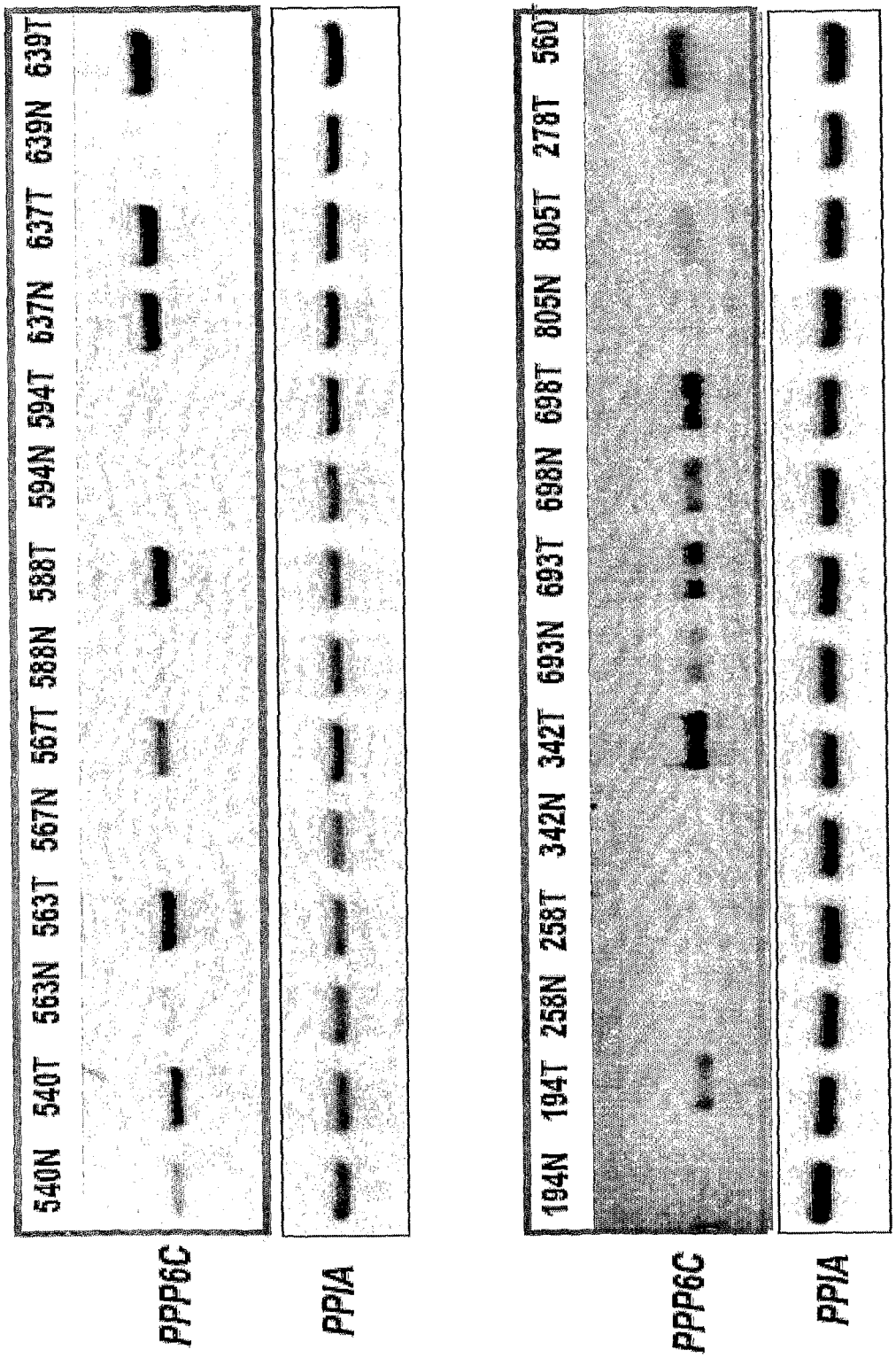
Figure 8E:
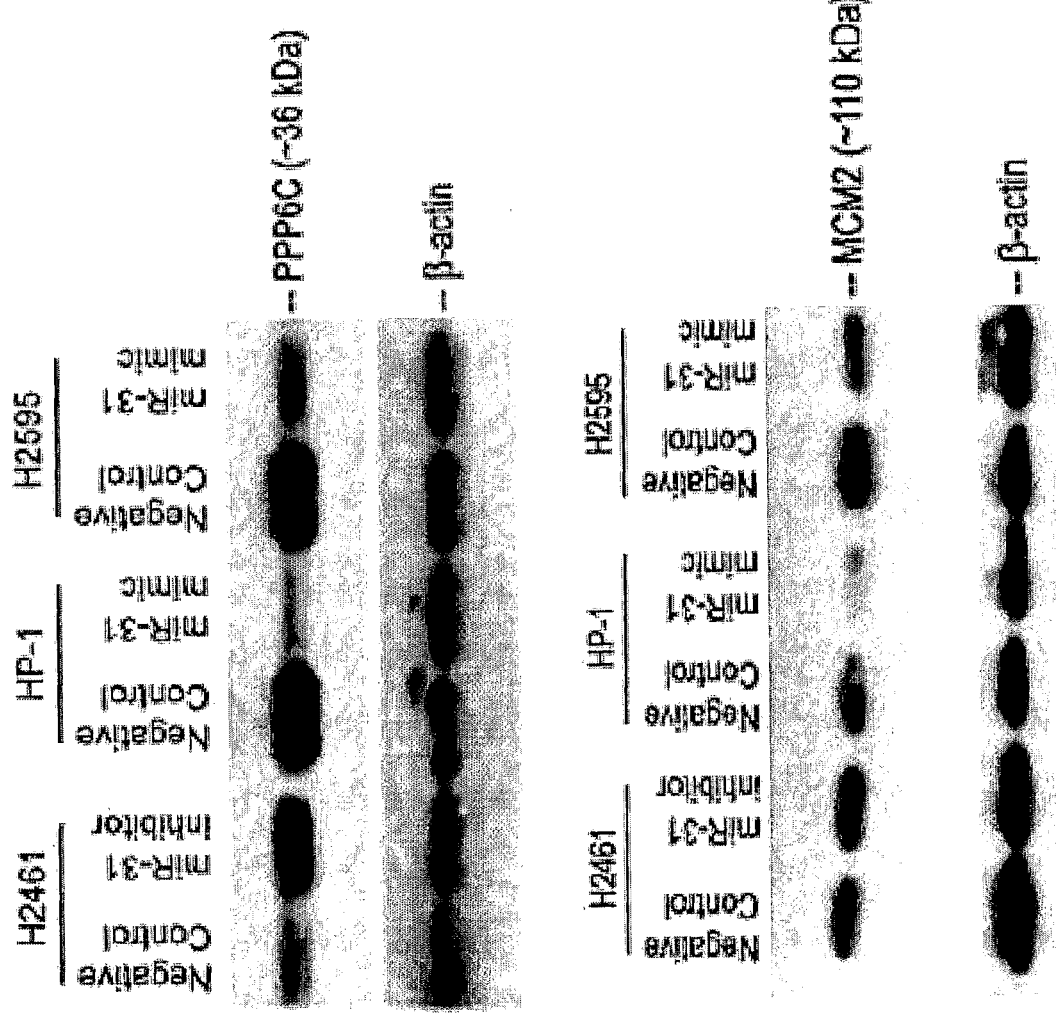

Validation of Protein Phosphatase 6 as a miR-31 Target and a Diagnostic Marker for Malignant Mesothelioma Among predicted miR-31 targets PPP6C is one of the most intriguing due to the established links with cell cycle regulation (Bastiens and Ponstingl, J Cell Sci 1996; 109:2865-2874), apoptosis and chemo-resistance (MacKeigan et al., Nat Cell Biol 2005; 7:591-600), resistance to radiation (Mi et al., PLoS One 2009; 4:e4395), and regulation of chromosome segregation (Goshima et al., Embo J 2003; 22:2752-2763). Since all these PPP6C properties suggested a principal role for the gene in progression of malignant mesothelioma, a cancer distinguished with multiple chromosomal instability (Ivanov et al., Int J Cancer 2009; 124:589-599) and resistance to common therapies, the possibility that PPP6C is indeed a direct miR-31 target was investigated. PPP6C possesses in its 3'-UTR three predicted binding sites for miR-31 (FIG. 8A). In the expression microarray study on HP-1, PPP6C was consistently down-regulated by miR-31 introduction (FIG. 8B). A RT-PCR analysis of malignant mesothelioma cells transfected with miR-31 or its inhibitor showed that expression of endogenous PPP6C was responsive to the miR-31 status in both cell lines. Suppression of endogenous miR-31 in H2461 caused up-regulation of endogenous PPP6C, suggesting that the observed relation between miR-31 and PPP6C is highly reproducible and biologically relevant (FIGS. 8C and E). Another potential miR-31 target, MCM2, is suppressed by miR-31, as demonstrated on the protein level (FIG. 8E).

Since PPP6C has not been yet associated with malignant mesothelioma, its expression in clinical tumor specimens supplemented with matched controls was analyzed. This study showed that expression of this gene was profoundly elevated in ~86% of malignant mesothelioma specimens as compared to matched normal healthy peritonea, fitting the pro-tumorigenic role of PPP6C in malignant mesothelioma (FIG. 8D).

Example 8

In Vivo Proof of Principle that Upregulation of miR-31 Decreases Tumor Growth and Invasion A powerful lentiviral expression vectors with specific miR-31 sequence are used to enhance the expression of miR-31 in order to investigate its effect on the proliferation and metastasis of H-meso mesothelioma cells, which grow well in the flanks of nude mice. H-meso cells are ex-vivo infected with lentiviral particles and then transplanted into the flanks of the animals.

Example 8.I

Vector Construction of miR-31

The miR-31 expression construct consists of native stem loop and 200-400 base pairs of upstream and downstream flanking genomic sequence. The genomic DNA fragment containing the hsa-miR-31 locus situated at chromosome 9 (9p21) plus 100-200 bp upstream and 100-200 bp downstream flanking genomic sequences from the 88 bp miR-31, is amplified and cloned into a FIV-based pMIF-cGFP-Zeo-miR lenti-vector (System Biosciences). A scrambled negative control is also generated. A standard Lipofectamine protocol (Invitrogen) is used to generate Infectious lenti-viral particles using pPACKF1 lenti-viral packaging mix (System Biosciences) for both LENTI.31 and LENTI.scrambled and viral titer is calculated. The produced infectious lenti-viral particle is introduced into the target cells.

Example 8.II

In Vivo Assays for H-Meso Tumor Growth and Metastasis

H-meso cells ($5 \times 10^6$) transfected with Lenti.31 or Lenti.scrambled (at a MOI of 50) are implanted subcutaneously into the flank of nude mice (6 in each group, male BALB/c nu/nu, 4-6 weeks), and H-meso cells treated with phosphate-buffered saline are used as a mock control. Tumor growth is monitored with tumor volume, which is calculated as described: V (mm3)=width$^2$ (mm$^2$)×length (mm)/2. The mice are sacrificed six weeks later, and the lungs are removed.

Consecutive sections are made for every tissue block of the lung and stained with hematoxylin-eosin. The incidence and classification of lung metastasis are calculated and evaluated independently by two pathologists. Based on the number of H-meso cells in the maximal section of the metastatic lesion, the lung metastases are classified into four grades: grade I, <20 cells; grade II, 20-50 cells; grade III, 50-100 cells; and grade IV, >100 cells.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It should be understood that the detailed description and specific examples, while indicating preferred embodiments of the invention, are given by way of illustration only, since various changes and modifications within the spirit and scope of the invention will become apparent to those skilled in the art from this detailed description.

The invention claimed is:

1. A method of treating malignant mesothelioma, inhibiting progression of malignant mesothelioma or decreasing malignant mesothelioma growth and invasion comprising administering to a human subject in need thereof a composition comprising a human miR-31 nucleic acid comprising SEQ ID NO: 1.

2. The method claim 1, further comprising administering at least one additional therapy.

3. The method of claim 2, wherein said at least one additional therapy is administration of a chemotherapeutic agent.

4. The method of claim 3, wherein said chemotherapeutic agent is selected from the group consisting of 5-fluorouracil, doxorubicine, mitomycin c, etoposide, carboplatin and cyclophosphamide.

5. The method of claim 2, wherein said at least one additional therapy is administration of a small molecule or antibody.

6. The method of claim 5, wherein said small molecule or antibody is selected from the group consisting of vorinostat, a PI3 kinase inhibitor, a mTOR inhibitor, a proteosome inhibitor, a vascular targeting agent and an angiogenesis inhibitor.

7. The method of claim 2, wherein said at least one additional therapy further comprises radiation therapy.

8. The method of claim 2, wherein said at least one additional therapy further comprises adjuvant immunological treatment.

9. The method of claim 8, wherein said adjuvant immunological treatment is selected from a group consisting of interferon and interleukin.

10. The method of claim 1, wherein said administering results in reduction of tumor size.

11. The method of claim 1, wherein said administering results in reduction of tumor number.

12. The method of claim 1, wherein said administering prevents an increase in tumor size.

13. The method of claim 1, wherein said administering prevents an increase in tumor number.

14. The method of claim 1, wherein said administering prevents metastatic progression.

15. The method of claim 1, wherein said administering slows metastatic progression.

16. The method of claim 1, wherein said administering extends overall survival time of the subject.

17. The method of claim 1, wherein said administering extends progression-free survival of the subject.

18. The method of claim 1, wherein said nucleic acid comprises a modified nucleobase.

* * * * *

SEQUENCE LISTING

<160> NUMBER OF SEQ ID NOS: 30

<210> SEQ ID NO 1
<211> LENGTH: 21
<212> TYPE: RNA
<213> ORGANISM: human

<400> SEQUENCE: 1
aggcaagaug cuggcauagc u                                              21

<210> SEQ ID NO 2
<211> LENGTH: 71
<212> TYPE: RNA
<213> ORGANISM: human

<400> SEQUENCE: 2
ggagaggagg caagaugcug gcauagcugu ugaacuggga accugcuaug ccaacauauu    60
gccaucuuuc c                                                         71

<210> SEQ ID NO 3
<211> LENGTH: 17
<212> TYPE: DNA
<213> ORGANISM: Artificial sequence
<220> FEATURE:
<223> OTHER INFORMATION: Synthetic

<400> SEQUENCE: 3
tgaccgaggc aagatgc                                                   17

<210> SEQ ID NO 4
<211> LENGTH: 55
<212> TYPE: DNA
<213> ORGANISM: Artificial sequence
<220> FEATURE:
<223> OTHER INFORMATION: Synthetic

<400> SEQUENCE: 4
gtcgtatcca gtgcagggtc cgaggtattc gcactggata cgacagctat gcctg         55

<210> SEQ ID NO 5
<211> LENGTH: 16
<212> TYPE: DNA
<213> ORGANISM: Artificial sequence
<220> FEATURE:
<223> OTHER INFORMATION: Synthetic

<400> SEQUENCE: 5
gtgcagggtc cgaggt                                                    16

```
<210> SEQ ID NO 6
<211> LENGTH: 21
<212> TYPE: DNA
<213> ORGANISM: Artificial sequence
<220> FEATURE:
<223> OTHER INFORMATION: Synthetic

<400> SEQUENCE: 6
cttgagggtc ctatggagtc a                                              21

<210> SEQ ID NO 7
<211> LENGTH: 20
<212> TYPE: DNA
<213> ORGANISM: Artificial sequence
<220> FEATURE:
<223> OTHER INFORMATION: Synthetic

<400> SEQUENCE: 7
gccagtcctt cgtgtattgc                                                20

<210> SEQ ID NO 8
<211> LENGTH: 20
<212> TYPE: DNA
<213> ORGANISM: Artificial sequence
<220> FEATURE:
<223> OTHER INFORMATION: Synthetic

<400> SEQUENCE: 8
gaatcccgta gcttccctac                                                20

<210> SEQ ID NO 9
<211> LENGTH: 19
<212> TYPE: DNA
<213> ORGANISM: Artificial sequence
<220> FEATURE:
<223> OTHER INFORMATION: Synthetic

<400> SEQUENCE: 9
cgggtcccga tttagaagg                                                 19

<210> SEQ ID NO 10
<211> LENGTH: 20
<212> TYPE: DNA
<213> ORGANISM: Artificial sequence
<220> FEATURE:
<223> OTHER INFORMATION: Synthetic

<400> SEQUENCE: 10
cctgctgtgc actagatctc                                                20

<210> SEQ ID NO 11
<211> LENGTH: 19
<212> TYPE: DNA
<213> ORGANISM: Artificial sequence
<220> FEATURE:
<223> OTHER INFORMATION: Synthetic

<400> SEQUENCE: 11
agggctccca ctgattctg                                                 19

<210> SEQ ID NO 12
<211> LENGTH: 21
<212> TYPE: DNA
<213> ORGANISM: Artificial sequence
<220> FEATURE:
<223> OTHER INFORMATION: Synthetic
```

-continued

<400> SEQUENCE: 12
gttatgctgc attccagatg g                                              21

<210> SEQ ID NO 13
<211> LENGTH: 21
<212> TYPE: DNA
<213> ORGANISM: Artificial sequence
<220> FEATURE:
<223> OTHER INFORMATION: Synthetic

<400> SEQUENCE: 13
gtaatgcttc caggtctatg c                                              21

<210> SEQ ID NO 14
<211> LENGTH: 20
<212> TYPE: DNA
<213> ORGANISM: Artificial sequence
<220> FEATURE:
<223> OTHER INFORMATION: Synthetic

<400> SEQUENCE: 14
cacatcctct ccagcatctg                                                20

<210> SEQ ID NO 15
<211> LENGTH: 21
<212> TYPE: DNA
<213> ORGANISM: Artificial sequence
<220> FEATURE:
<223> OTHER INFORMATION: Synthetic

<400> SEQUENCE: 15
accttctgcc atgattgtga g                                              21

<210> SEQ ID NO 16
<211> LENGTH: 20
<212> TYPE: DNA
<213> ORGANISM: Artificial sequence
<220> FEATURE:
<223> OTHER INFORMATION: Synthetic

<400> SEQUENCE: 16
gaatgctgcg gagaaacatg                                                20

<210> SEQ ID NO 17
<211> LENGTH: 21
<212> TYPE: DNA
<213> ORGANISM: Artificial sequence
<220> FEATURE:
<223> OTHER INFORMATION: Synthetic

<400> SEQUENCE: 17
cactgtgcag ataaagggaa c                                              21

<210> SEQ ID NO 18
<211> LENGTH: 20
<212> TYPE: DNA
<213> ORGANISM: Artificial sequence
<220> FEATURE:
<223> OTHER INFORMATION: Synthetic

<400> SEQUENCE: 18
aaacgtagca gtcaggaggc                                                20

<210> SEQ ID NO 19

```
<211> LENGTH: 20
<212> TYPE: DNA
<213> ORGANISM: Artificial sequence
<220> FEATURE:
<223> OTHER INFORMATION: Synthetic

<400> SEQUENCE: 19
tcaacagcgg gaataacaca                                          20

<210> SEQ ID NO 20
<211> LENGTH: 20
<212> TYPE: DNA
<213> ORGANISM: Artificial sequence
<220> FEATURE:
<223> OTHER INFORMATION: Synthetic

<400> SEQUENCE: 20
tggggatcct tacaaagtgc                                          20

<210> SEQ ID NO 21
<211> LENGTH: 20
<212> TYPE: DNA
<213> ORGANISM: Artificial sequence
<220> FEATURE:
<223> OTHER INFORMATION: Synthetic

<400> SEQUENCE: 21
cttcgtgtag tcctgctgcc                                          20

<210> SEQ ID NO 22
<211> LENGTH: 20
<212> TYPE: DNA
<213> ORGANISM: Artificial sequence
<220> FEATURE:
<223> OTHER INFORMATION: Synthetic

<400> SEQUENCE: 22
ccttccgagt ggaaagagtg                                          20

<210> SEQ ID NO 23
<211> LENGTH: 20
<212> TYPE: DNA
<213> ORGANISM: Artificial sequence
<220> FEATURE:
<223> OTHER INFORMATION: Synthetic

<400> SEQUENCE: 23
aactattcct gcccgcctat                                          20

<210> SEQ ID NO 24
<211> LENGTH: 20
<212> TYPE: DNA
<213> ORGANISM: Artificial sequence
<220> FEATURE:
<223> OTHER INFORMATION: Synthetic

<400> SEQUENCE: 24
agtatgtgga aatagcgcgg                                          20

<210> SEQ ID NO 25
<211> LENGTH: 20
<212> TYPE: DNA
<213> ORGANISM: Artificial sequence
<220> FEATURE:
<223> OTHER INFORMATION: Synthetic

<400> SEQUENCE: 25
```

```
aaaaatgggt cagcaggatg                                                20

<210> SEQ ID NO 26
<211> LENGTH: 21
<212> TYPE: DNA
<213> ORGANISM: Artificial sequence
<220> FEATURE:
<223> OTHER INFORMATION: Synthetic

<400> SEQUENCE: 26
tctgagcact ggagagaaag g                                              21

<210> SEQ ID NO 27
<211> LENGTH: 21
<212> TYPE: DNA
<213> ORGANISM: Artificial sequence
<220> FEATURE:
<223> OTHER INFORMATION: Synthetic

<400> SEQUENCE: 27
ggaaaacatg gaacccaaag g                                              21

<210> SEQ ID NO 28
<211> LENGTH: 21
<212> TYPE: RNA
<213> ORGANISM: human

<400> SEQUENCE: 28
cugaaaugcu gccucuugcc u                                              21

<210> SEQ ID NO 29
<211> LENGTH: 21
<212> TYPE: RNA
<213> ORGANISM: human

<400> SEQUENCE: 29
ugcugcaugu agcucuugcu u                                              21

<210> SEQ ID NO 30
<211> LENGTH: 21
<212> TYPE: RNA
<213> ORGANISM: human

<400> SEQUENCE: 30
ucugccaucu cuguuuugcc u                                              21
```